US010792178B2

(12) United States Patent
Alvarez et al.

(10) Patent No.: US 10,792,178 B2
(45) Date of Patent: Oct. 6, 2020

(54) JOINT STABILIZING ORTHOPEDIC DEVICE

(71) Applicants: Christian A. Alvarez, Camarillo, CA (US); Robert B. Murray, III, Ventura, CA (US); David Nelson, Camarillo, CA (US); John Lucas, Camarillo, CA (US)

(72) Inventors: Christian A. Alvarez, Camarillo, CA (US); Robert B. Murray, III, Ventura, CA (US); David Nelson, Camarillo, CA (US); John Lucas, Camarillo, CA (US)

( * ) Notice: Subject to any disclaimer, the term of this patent is extended or adjusted under 35 U.S.C. 154(b) by 490 days.

(21) Appl. No.: 15/668,579

(22) Filed: Aug. 3, 2017

(65) Prior Publication Data
US 2018/0036161 A1 Feb. 8, 2018

Related U.S. Application Data

(60) Provisional application No. 62/371,113, filed on Aug. 4, 2016.

(51) Int. Cl.
| *A61F 5/00* | (2006.01) |
| *A61F 5/01* | (2006.01) |
| *A63B 21/04* | (2006.01) |
| *A63B 21/055* | (2006.01) |
| *A63B 21/00* | (2006.01) |
| *A63B 23/12* | (2006.01) |
| *A63B 23/04* | (2006.01) |

(52) U.S. Cl.
CPC ........ *A61F 5/0118* (2013.01); *A63B 21/0442* (2013.01); *A63B 21/0552* (2013.01); *A63B 21/4025* (2015.10); *A63B 23/1245* (2013.01); *A63B 21/00061* (2013.01); *A63B 21/00065* (2013.01); *A63B 21/4005* (2015.10); *A63B 21/4007* (2015.10); *A63B 21/4017* (2015.10); *A63B 23/0494* (2013.01); *A63B 2225/09* (2013.01)

(58) Field of Classification Search
None
See application file for complete search history.

(56) References Cited

U.S. PATENT DOCUMENTS

| 4,735,198 | A | * | 4/1988 | Sawa | A61F 13/146 |
| | | | | | 128/878 |
| 5,458,565 | A | | 10/1995 | Tillinghast | |
| 5,628,725 | A | | 5/1997 | Ostergard | |
| 5,857,990 | A | * | 1/1999 | Maas | A61F 5/3738 |
| | | | | | 602/20 |
| 6,106,493 | A | * | 8/2000 | Rozell | A61F 5/3738 |
| | | | | | 128/874 |
| 6,303,111 | B1 | * | 10/2001 | Maurer | A61L 9/01 |
| | | | | | 424/76.1 |
| 6,306,111 | B1 | | 10/2001 | Dean | |

(Continued)

*Primary Examiner* — Kim M Lewis
(74) *Attorney, Agent, or Firm* — Procopio, Cory, Hargreaves & Savitch LLP.

(57) ABSTRACT

An orthopedic device configured to provide support and/or resistance to a joint. The orthopedic device is adjustable and lightweight and configured to permit a substantial full range of motion of the joint. The orthopedic device can comprise a torso portion, an upper arm portion, and a support system, wherein at least the support system is adapted to mimic part of the muscular system structure and function of the muscles that are used during the range of motion of the joint.

17 Claims, 14 Drawing Sheets

(56) References Cited

U.S. PATENT DOCUMENTS

| | | | | |
|---|---|---|---|---|
| 6,398,746 | B2* | 6/2002 | Bramlage | A61F 5/24 128/869 |
| 10,085,875 | B2* | 10/2018 | Fair | A61F 5/373 |
| 2009/0149787 | A1* | 6/2009 | Scott | A61F 5/3723 602/4 |
| 2011/0034841 | A1* | 2/2011 | Richard | A61F 5/3746 602/4 |
| 2012/0041352 | A1* | 2/2012 | Ostergard | A61F 5/3723 602/20 |
| 2012/0253251 | A1* | 10/2012 | Thornton | A61F 5/028 602/19 |

* cited by examiner

FIG. 10
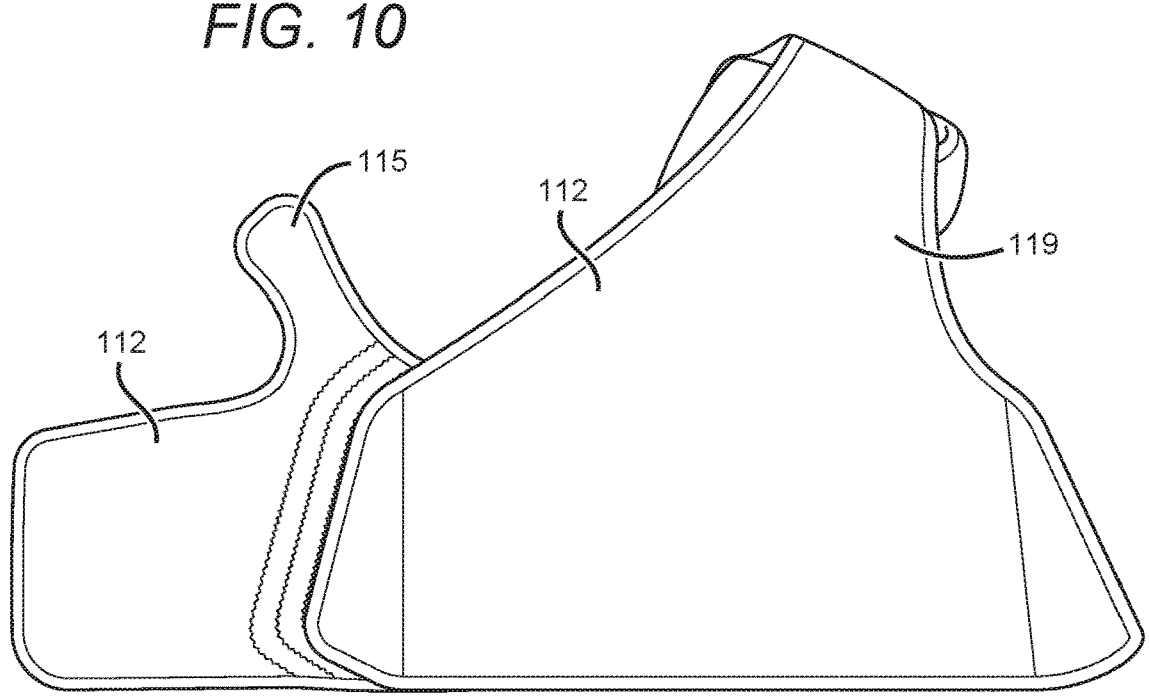
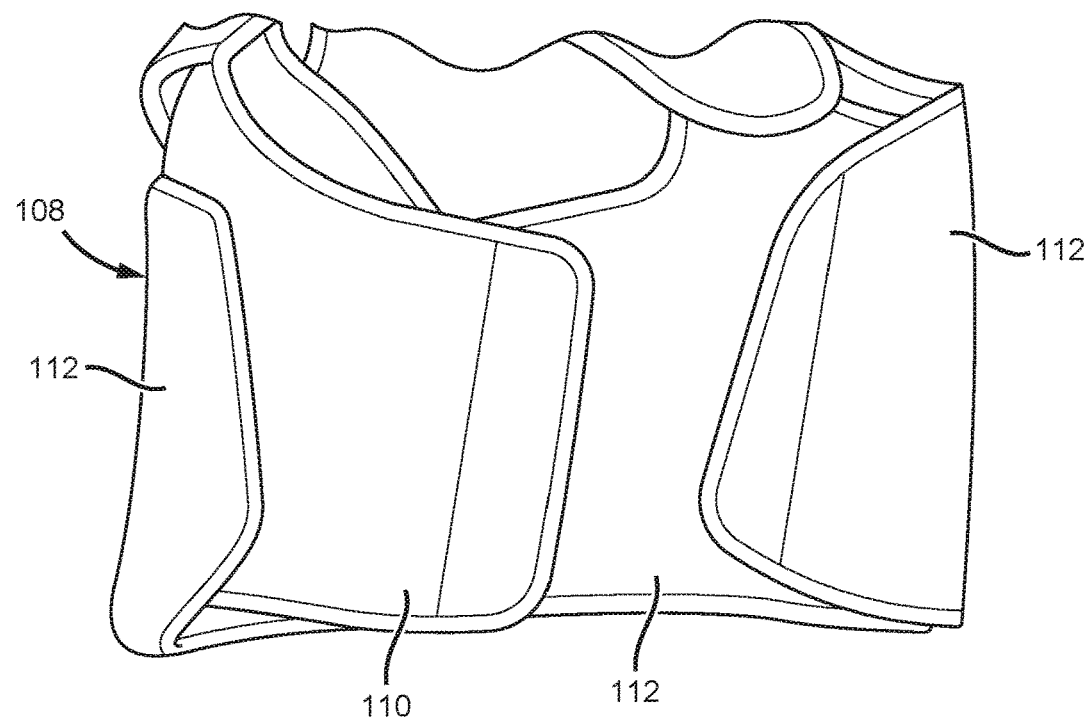
FIG. 11

JOINT STABILIZING ORTHOPEDIC DEVICE

RELATED APPLICATION

This application claims the benefit of priority of U.S. Provisional Application Ser. No. 62/371,113, filed on Aug. 4, 2016. The contents of Ser. No. 62/371,113 including its drawings, schematics, diagrams, and written description, are hereby incorporated in their entirety by reference.

BACKGROUND

Field

This disclosure generally relates to an orthopedic device and method of using the same. More particularly, the disclosure relates to a lightweight, adjustable joint stabilizing orthopedic device configured to provide support and resistance to a joint.

Description of the Related Art

There are often times when an athlete and/or a person sustains an injury which is not severe enough to justify discontinuing the sport and/or activity until the injury is healed but which is painful and could be susceptible to cause a serious injury, if continuing to play the sport and/or conduct the activity.

Injured athletes and people often employ taping of the injured area to prevent further injury. Although taping can guard against further serious injury, taping still has some drawbacks. For example, there is quite an art to taping and experienced trainers, doctors, and/or other medical personnel have the training and knowledge to properly apply tape to an injured area. In some instances where the injured area is not easily accessible to the injured person, such as the shoulder region, it is difficult for the injured person to apply tape themselves.

Some joint injuries are treated by therapeutic tapings by skilled practitioners in a fashion that works to stabilize rather than immobilize the motion about the joint. With these tapings, the joint may still be articulated in activities that require a full or nearly full range of motion with minimal discomfort and without additional injury to the joint. However, each taping is inherently temporary and typically requires the skill and access of a person other than the injured person. In addition, the tapings must be repeatedly removed and redone over the course of the healing of the joint injury and with each removal of the taping, the skin about the joint area is adversely affected. In situations where the injured person continues activities that draw upon the full range or nearly full range of motion of the joint, the taping can become stretched and lose some of its stabilizing effectiveness, or could be removed due to continued participation in the activity, and could ultimately become ineffective. In competitive activities, this may be remedied by a re-taping. However, proper re-taping can be time consuming, and in competitive activities, time may be limited such that re-taping may not be done properly and could result in further injury. Additionally, tape may not be resistant to environmental factors, such as, rain, snow, mud, dirt, etc., which could negatively impact the taping.

Some joint injuries are treated by the application of an adjustable body harness, brace or sling. For example, a shoulder brace having an arm portion attached to a torso portion used for anchoring, and straps for anchoring the upper arm to the torso portion or otherwise significantly reducing the rotation of the arm away from the torso may be used. It is common throughout these body harnesses and braces that abduction, that is, the extending of the arm away from the body, is significantly restricted and accordingly, these harnesses and braces do not provide for a full or nearly-full range of motion about the injured shoulder joint.

The disclosure is a joint stabilizing orthopedic device that is lightweight, adjustable, reusable, and adapted to provide support and resistance to a joint. The present disclosure addresses these needs and provides further related advantages.

SUMMARY

The disclosure provides various aspects of a joint stabilizing orthopedic device configured to provide support and/or resistance to limb within a joint. The different aspects comprise elements to allow the orthopedic device to provide support and/or resistance to a limb within the joint. The orthopedic device provides support and/or stability to a limb within a joint allowing for substantially a full range of motion of the limb within the joint. The support provided by the orthopedic device assists in proper alignment of the limb within the joint, as well as substantially maintaining proper alignment of the joint during the range of motion of the joint. The orthopedic device is configured to be lightweight, adjustable, reusable, such that an athlete and/or person can continue participating in sports and/or other activities. The disclosure overcomes the drawbacks of conventional taping and allows for the full or substantially full range of motion for a limb within a joint that is not present in conventional harnesses.

In one aspect of the disclosure, as broadly described herein, an orthopedic device is disclosed that provides support and/or stability to an upper arm within a shoulder joint, comprising a torso portion, an upper arm portion, and a support system. The torso portion comprising a belt portion for securing the orthopedic device to a torso. The belt portion can comprise a front portion and a back portion, wherein the front and back portions are adapted to be removably coupled to each other. The torso portion further comprising a shoulder portion having a shoulder band extending towards the back portion of the belt portion, such that the shoulder band is removably coupled to part of the back portion of the belt portion. The upper arm portion can comprise an inner upper arm portion and an outer upper arm portion, wherein the inner and outer upper arm portions secure the orthopedic device to the upper arm. At least one or both of the inner and outer upper arm portions can be removably coupled to each other to secure the orthopedic device to the upper arm. The upper arm portion is coupled to the torso portion, proximate the shoulder portion. The support system is configured to be removably coupled to at least part of the torso portion, part of the upper arm portion, part of the shoulder portion, and/or a combination thereof. In some aspects, the support system comprises at least one strap configured to stabilize the upper arm within the shoulder joint. In some aspects, the support system comprises at least one resistance band and at least one strap, wherein the at least one resistance band is received by at least one strap. The at least one strap and at least one resistance band are configured to stabilize the upper arm within the shoulder joint, such that the joint maintains proper alignment through the range of motion of the upper arm within the joint. The at least one strap and at least one resistance band can also be configured to provide resistance training to the joint. The at least one strap can be removably coupled to part of the torso portion, part of the upper arm portion, and/or a combination thereof, such that the orthopedic device provides support to the shoulder joint. The orthopedic devices allows for substantially a full range of motion of the shoulder joint. The support provided by the orthopedic device assists in proper alignment of the upper arm within the joint, as well as substantially maintaining proper alignment of the joint during the range of motion of the upper arm within the joint.

In another aspect, an orthopedic device comprises a torso portion comprising a belt portion and a shoulder portion, wherein the belt portion comprises a plurality of belt portion panels, wherein the plurality of belt portion panels are adapted to be removably coupled to adjust the size of the belt portion. The shoulder portion comprises at least one front shoulder band portion and a back shoulder band portion, wherein the at least one front shoulder band portion is removably coupled to the belt portion. The back shoulder band portion extends from the belt portion and is fixedly attached to the at least one front shoulder band portion. The orthopedic device further comprises an upper arm portion coupled to the shoulder portion. The upper arm portion comprises an inner upper arm portion, an outer upper arm portion, and at least one opening such that the upper arm portion can move with respect to the shoulder portion. The orthopedic device further comprises a support system received by at least part of the shoulder portion and/or part of the upper arm portion, and removably coupled to part of the belt portion, wherein the support system is adapted to exert a force proximate the shoulder portion to promote biomechanical stability. In some aspects, the support system comprises one or more straps, at least one resistance band received by the one or more straps, and a resistance band housing, wherein part of the at least one resistance band is received by the resistance band housing such that the positioning of the at least one resistance band and/or one or more straps is substantially maintained by the resistance band housing. In some aspects, the support system comprises at least a first strap and at least a second strap, wherein the first strap is coupled to part of the upper arm portion and the belt portion, and the second strap is coupled to part of the shoulder portion and the belt portion. The configuration of the first and/or second straps can be adjusted such that the resistance provided by the respective at least one resistance bands can be increased and/or decreased.

This has outlined, rather broadly, the features and technical advantages of the disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further objects and advantages, will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

FIG. 10 is another partial view of the torso portion according to an aspect of the disclosure.

FIG. 11 is a front view of the belt portion according to an aspect of the disclosure.

DETAILED DESCRIPTION

Figure 1:
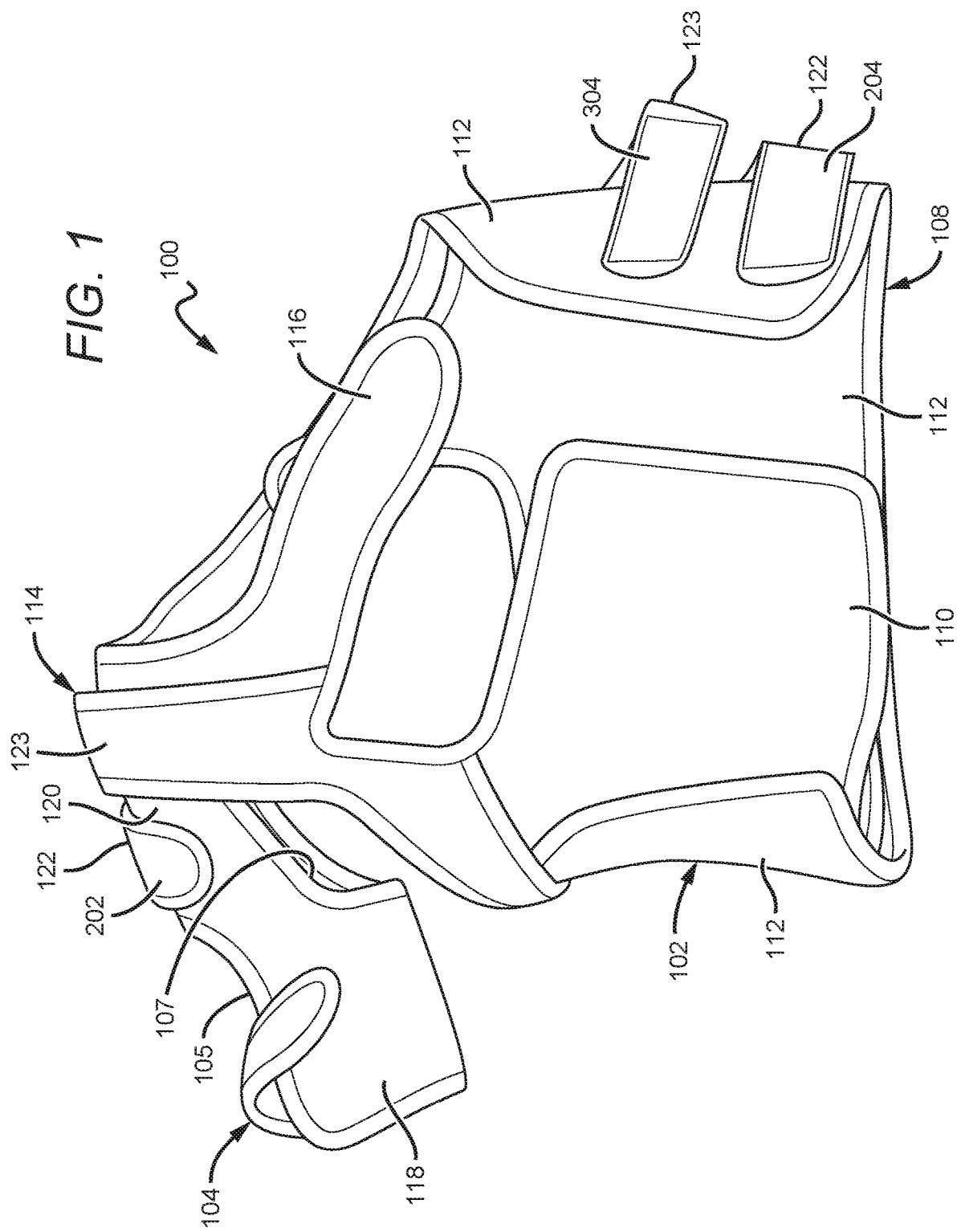
FIG. 1 is a perspective view of an orthopedic device according to an aspect of the disclosure.

The disclosure described herein is directed to different aspects of a joint stabilizing orthopedic device that in some aspects is configured to provide support and/or resistance to a joint. The different aspects comprise elements to allow the orthopedic device to provide support and/or resistance to the joint. The orthopedic device provides support and/or stability to a joint allowing for substantially a full range of motion of the joint. The support provided by the orthopedic device assists in proper alignment of the limb within the joint, as well as substantially maintaining proper alignment of the joint during the range of motion of the joint. The orthopedic device is configured to be lightweight, adjustable, reusable, such that an athlete and/or person can continue participating in sports and/or other activities. The orthopedic device can be used for stabilizing various joints, such as but not limited to, the shoulder, knee, ankle, wrist, and/or lower back. The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. It will be apparent, however, to those skilled in the art that these concepts may be practiced without these specific details. In some instances, well-known structures and components are shown in block diagram form in order to avoid obscuring such concepts. As described herein, the use of the term "and/or" is intended to represent an "inclusive OR", and the use of the term "or" is intended to represent an "exclusive OR".

The orthopedic device can comprise many different materials and can be used in many different applications such as, but not limited to, resistance exercises and/or rehabilitate an injured and/or weakened joint. The orthopedic device according to the disclosure can be arranged in many different ways with many different components, and is generally arranged to provide support to a joint. In one aspect, as broadly described herein, the orthopedic device provides support and/or stability to an upper arm within a shoulder joint, the orthopedic device comprising a torso portion, an upper arm portion, and a support system. The torso portion comprising a belt portion for securing the orthopedic device to a torso. The belt portion can comprise a front portion and a back portion, wherein the front and back portions are adapted to be removably coupled to each other. The torso portion further comprising a shoulder portion having a shoulder band extending towards the back portion of the belt portion, such that the shoulder band is removably coupled to part of the back portion of the belt portion. The upper arm portion can comprise an inner upper arm portion and an outer upper arm portion, wherein the inner and outer upper arm portions are configured to secure the orthopedic device to the upper arm. At least one or both of the inner and outer upper arm portions can be removably coupled to each other to secure the orthopedic device to the upper arm. The upper arm portion is coupled to the torso portion, proximate the shoulder portion. The support system is configured to be coupled to at least one of the torso portion, the upper arm portion, the shoulder portion and/or a combination thereof. In some aspects, the support system comprises at least one strap configured to stabilize the upper arm within the shoulder joint. In some aspects, the support system comprises at least one resistance band and at least one strap, wherein the at least one resistance band is received by at least one strap. The at least one strap can be removably coupled to the torso portion, the upper arm portion, the shoulder portion and/or a combination thereof, such that the orthopedic device provides support to the shoulder joint. The orthopedic devices allows for substantially a full range of motion of the shoulder joint. The support provided by the orthopedic device assists in proper alignment of the upper arm within the joint, as well as substantially maintaining proper alignment of the joint during the range of motion of the joint.

In another aspect, an orthopedic device comprises a torso portion comprising a belt portion and a shoulder portion, wherein the belt portion comprises a plurality of belt portion panels, wherein the plurality of belt portion panels are adapted to be removably coupled to adjust the size of the belt portion. The shoulder portion comprises at least one front shoulder band portion and a back shoulder band portion, wherein the at least one front shoulder band portion is removably coupled to the belt portion. The back shoulder band portion extends from the belt portion and is fixedly attached to the at least one front shoulder band portion. The orthopedic device further comprises an upper arm portion coupled to the shoulder portion. The upper arm portion comprises an inner upper arm portion, an outer upper arm portion, and at least one opening such that the upper arm portion can move with respect to the shoulder portion. The orthopedic device further comprises a support system received by at least part of the shoulder portion and/or part of the upper arm portion, and removably coupled to part of the belt portion, wherein the support system is adapted to exert a force proximate the shoulder portion to promote biomechanical stability. In some aspects, the support system comprises one or more straps, at least one resistance band received by the one or more straps, and a resistance band housing, wherein part of the at least one resistance band is received by the resistance band housing such that the positioning of the at least one resistance band and/or one or more straps is substantially maintained by the resistance band housing. In some aspects, the support system comprises at least a first strap and at least a second strap, wherein the first strap is coupled to part of the upper arm portion and the belt portion, and the second strap is coupled to part of the shoulder portion and the belt portion. The configuration of the first and/or second straps can be adjusted such that the resistance provided by the respective at least one resistance bands can be increased and/or decreased.

The orthopedic device of the disclosure can provide a number of additional advantages beyond those mentioned above. For example, the support system of the orthopedic device is adapted to provide resistance to the joint, wherein the orthopedic device can be used to strengthen and/or exercise the joint. The orthopedic device can be used to rehabilitate an injured and/or weakened joint. The at least one resistance band of the support system provides resistance to the joint which allows the joint to be exercised and/or strengthened. The orthopedic device can increase the rate of recovery and/or the rate of rehabilitation of the joint, due in part to the support system. The support system is adapted to mimic part of the muscular system structure and function of the muscles that are used during the range of motion of the joint, such as but not limited to the muscles of a rotator cuff. The orthopedic device not only stabilizes the joint, but continued and repeated exercise of the joint with the orthopedic device trains the muscles to maintain proper alignment of the joint such that the muscular system of the joint is strengthened and results in improved proper natural range of motion. The orthopedic device can improve muscle memory such that muscle-related tasks are easier to perform without conscious effort.

Some aspects of the orthopedic device according to the disclosure can be used to stabilize a joint when performing sports-related activities and/or non-sports-related activities. However, the disclosure is not intended to be limited to such aspects. As further described below, the orthopedic device can be arranged to allow the joint to be rehabilitated due to the at least one resistance band. The at least one resistance band provides some resistive force against the joint while in motion, such that the at least one resistance band allows the joint to be exercised and assist in strengthening the joint.

The disclosure is described herein with reference to certain aspects, but it is understood that the disclosure can be embodied in many different forms and should not be construed as limited to the aspects set forth herein. In particular, the disclosure is described below in regards to an orthopedic device that stabilizes a shoulder joint, but it is understood that the disclosure can be used to support and/or stabilize other joints. The components of the orthopedic device can have different shapes and sizes beyond those shown in the figures and/or discussed herein.

Although the terms first, second, etc. may be used herein to describe various elements or components, these elements or components should not be limited by these terms. These terms are only used to distinguish one element or component from another. Thus, a first element discussed herein could be termed a second element without departing from the teachings of the present application. It is understood that actual systems or fixtures embodying the disclosure can be arranged in many different ways with many more features and elements beyond what is shown in the figures.

It is to be understood that when an element or component is referred to as being "on" another element or component, it can be directly on the other element or intervening elements may also be present. Furthermore, relative terms such as "between", "within", "below", and similar terms, may be used herein to describe a relationship of one element or component to another. It is understood that these terms are intended to encompass different orientations of the device in addition to the orientation depicted in the figures.

Aspects of the disclosure are described herein with reference to illustrations that are schematic illustrations. As such, the actual thickness of elements can be different, and variations from the shapes of the illustrations as a result, for example, of manufacturing techniques and/or tolerances are expected. Thus, the elements illustrated in the figures are schematic in nature and their shapes are not intended to illustrate the precise shape of a region of a device and are not intended to limit the scope of the disclosure.

Figure 2:
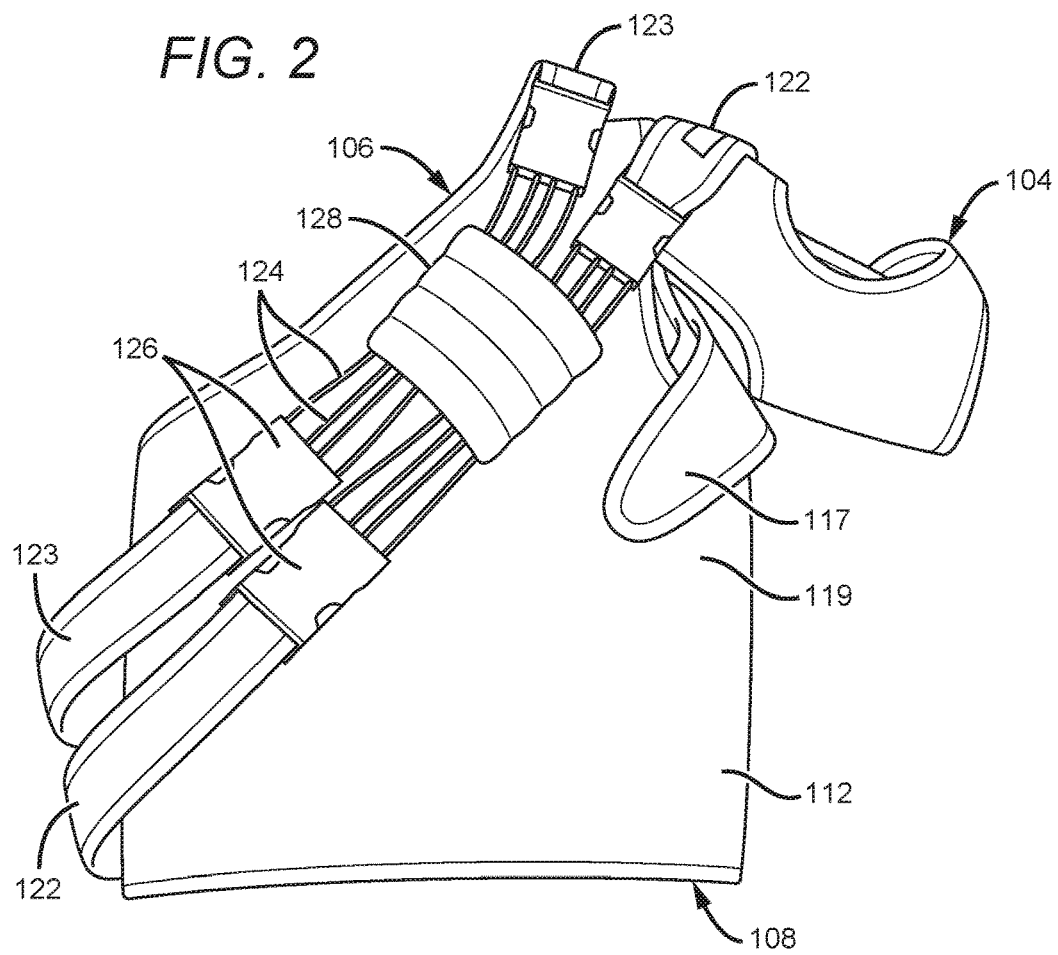
FIG. 2 is a rear view of the orthopedic device of FIG. 1.

FIGS. 1 and 2 show one aspect of an orthopedic device 100 according to the disclosure.

The orthopedic device 100 comprises a torso portion 102, an upper arm portion 104, and a support system 106. The torso portion 102 comprises a belt portion 108 for securing the orthopedic device 100 to a torso. The belt portion 108 can be comprised of a plurality of belt portions, for example, a front portion 110 and at least one back portion 112. The front and at least one back portions 110, 112 are adapted to be removably coupled to each other. The torso portion 102 further comprises a shoulder portion 114 having at least one shoulder band 116 extending towards the at least one back portion 112 of the belt portion 108, such that the at least one shoulder band 116 is removably coupled to part of the at least one back portion 112 of the belt portion 108. The upper arm portion 104 can comprise an inner upper arm portion 120 and an outer upper arm portion 118, wherein the inner and outer upper arm portions 120, 118 are adapted to secure the orthopedic device 100 to an upper arm. At least one or both of the inner and outer upper arm portions can be removably coupled to each other and/or itself to secure the orthopedic device 100 to the upper arm. The upper arm portion 104 is coupled to the torso portion 102, proximate the shoulder portion 114. The support system 106 is adapted to exert a force proximate the shoulder portion to promote biomechanical stability. The support system 106 is configured to be coupled to at least one of part of the torso portion 102, part of the upper arm portion 104, part of the shoulder portion 114, and/or a combination thereof. In some aspects, the support system 106 comprises at least one strap 122 configured to stabilize the upper arm within the shoulder joint. In some aspects, the support system 106 comprises at least one resistance band 124 and at least one strap 122, wherein the at least one resistance band 124 is configured to be received by the at least one strap 122. The at least one strap 122 and resistance band 124 are configured to stabilize the upper arm within the joint and provide resistance training to the joint. The at least one strap 122 can be removably coupled to at least one of part of the torso portion 102, part of the upper arm portion 104, part of the shoulder portion 114, and/or a combination thereof, such that the orthopedic device 100 provides support to the upper arm within the shoulder joint.

In the aspect of FIGS. 1 and 2, the orthopedic device 100 is configured to provide support to a right shoulder joint. However, the orthopedic device 100 is not intended to be limited to be used to support a right shoulder joint. In other aspects, the orthopedic device can provide support to the left shoulder joint. In yet other aspects, the orthopedic device can be configured to provide support to other joints, such as but not limited to, knee, ankle, wrist, and/or lower back.

In some aspects, the orthopedic device 100 stabilizes an upper arm within the shoulder joint and reduces the stress of muscles that might be present due to injury and/or weakened muscles. The orthopedic device 100 is configured to mimic at least some of the surrounding muscles to relieve stress off the shoulder joint and assist to stabilize the shoulder joint.

FIGS. 3-11 show one aspect of a torso portion 102 according to the disclosure.

The torso portion 102 comprises a belt portion 108 that secures the orthopedic device to a torso region of a user, such as the waist. The belt portion 108 can comprise a plurality of belt portion panels that are removably coupled to secure the belt portion 108 to the torso of the user. The plurality of belt portion panels being removably coupled allows the size of the belt portion 108 to adjust for various sized torsos, such that the belt portion 108 is size adjustable. In some aspects, the belt portion 108 comprises a front belt portion 110 and at least one back belt portion 112, wherein the front and at least one back belt portions are configured to be removably coupled to each other. In the aspect of FIGS. 1 and 2, the belt portion 108 comprises a front belt portion 110, a first back belt portion 112, and a second back belt portion 112, wherein the front belt portion 110 is coupled to the first back belt portion 112, the first back belt portion 112 is coupled to the second back belt portion 112, and the second back belt portion 112 is coupled to the front belt portion 110. In some aspects, the back belt portion 112 can be comprise of one or more back belt portions and is not intended to be limited to the aspects disclosed herein. In yet some aspects, the front belt portion 110 can be comprised or one or more front belt portions and is not intended to be limited to be limited to the aspects disclosed herein.

Figure 3:
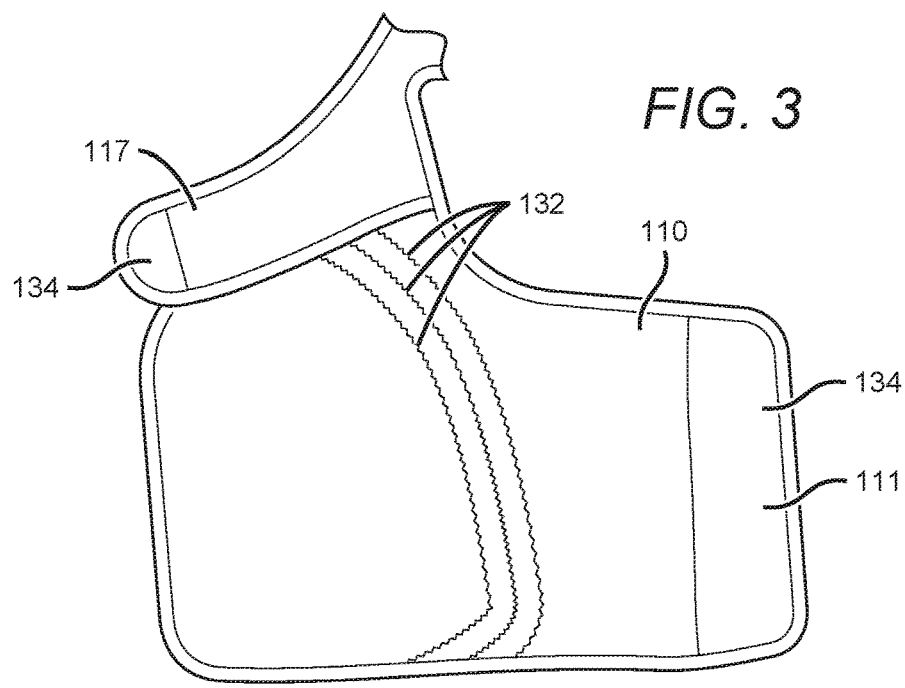
FIG. 3 is a partial view of a torso portion according to an aspect of the disclosure.

The front belt portion 110, as shown in FIG. 3, can comprise a front belt portion extension 111 that is adapted to be received by the first back belt portion 112. The extension 111 extends towards the first back belt portion 112, in order to couple the front belt portion 110 to the first back belt portion 112. The front belt portion 110 further comprises a mounting region 134 on an interior surface of the front belt portion 110 that is configured to be received by an exterior surface of the first back belt portion 112. The mounting region 134 can comprise a plurality of hooks (not shown), while the exterior surface of the first back belt portion 112 comprises a plurality of loops (not shown), such that the mounting region 134 can be removably coupled to the exterior surface of the first back belt portion 112. In some aspects, the mounting region 134 can be on the exterior surface, while the interior surface of the first back belt portion comprises a plurality of loops to receive the mounting region 134. The orthopedic device 100 can be configured in many different ways and is not intended to be limited to the aspects disclosed herein. The mounting region 134 is securely coupled to the first back belt portion 112 and substantially maintains the connection between the front belt portion 110 and the first back belt portion 112. In some aspects, the front belt portion extension 111 extends across the front part of the torso of the user and can be received by part of the first back belt portion 112. In some aspects, the belt portion 108 can comprise guidelines 132 on one or more of the plurality of belt portion panels to guide the coupling of the plurality of belt portion panels. The guidelines 132 provide a visual indicator as to where the parts of the belt portions 108 are to be connected to properly assemble the orthopedic device 100. In the aspect of FIG. 3, the front belt portion 110 comprises guidelines 132 to assist in the coupling of the second back belt portion 112 to the front belt portion 110. In some aspects, the guidelines 132 can also act as belt portion 108 size indicators, such that the size of the belt portion 108 can be adjusted by aligning the plurality of belt portion panels with respect to at least one of the guidelines 132. In some aspects, the guidelines 132 can be color coded such that the plurality of belt portion panels can be aligned with respect to one or more of the color coded guidelines. The plurality of belt portion panels can be coupled to each other using the guidelines 132 as a reference. However, the plurality of belt portion panels do not need to be aligned with the guidelines 132 to secure the belt portion 108 to the torso of a user. In some aspects, the plurality of belt portion panels can be coupled to each other without referencing the guidelines 132. The outer surfaces of the plurality of belt portion panels can comprise a plurality of loops, such that any part of the outer surface of the plurality of belt portion panels can receive a mounting region 134 of one of the plurality of belt portion panels, wherein the mounting region 134 comprises a plurality of hooks.

Figure 4:
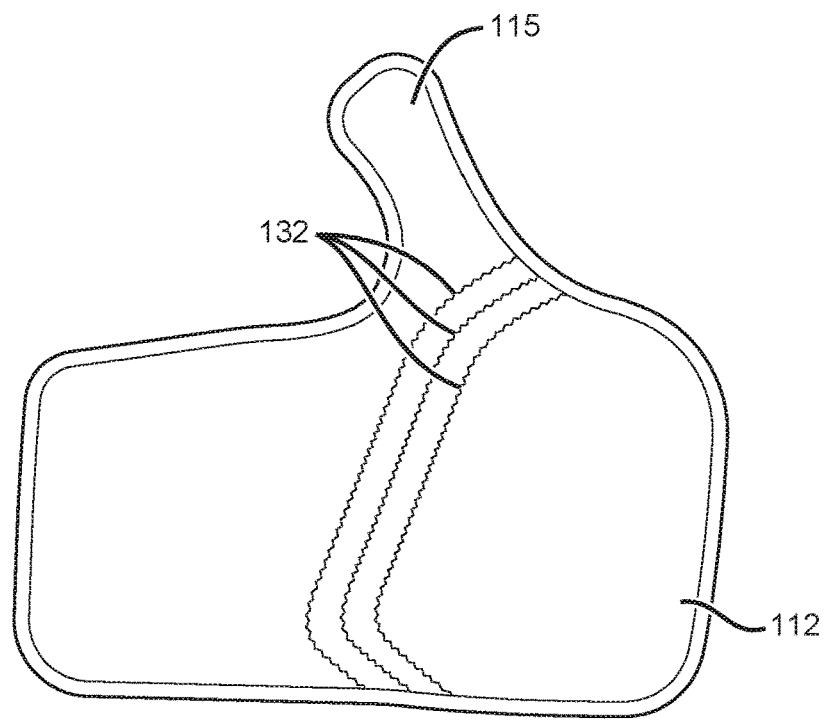
FIG. 4 is another partial view of the torso portion according to an aspect of the disclosure.

With reference to FIG. 4, the first back belt portion 112 can comprise a mount region 115 that extends from the first back belt portion 112 to receive the at least one shoulder band 116. In some aspects, the at least one shoulder band 116 can be removably coupled to any part of the back belt portion, and is not intended to be limited to be received by the mount region 115. The outer surface of the first back belt portion 112 can comprise a plurality of loops such that the mounting region 134 of the front belt portion 110 can be received by the first back belt portion 112. The first back belt portion 112 can also comprise the guidelines 132, similar to the front belt portion 110. The guidelines 132 of the first back belt portion 112 provide a visual indication as to where the second back belt portion 112 can be coupled to the first back belt portion 112. However, as stated above, the guidelines 132 can be used as a reference, such that it is not required for the second back belt portion 112 to be coupled to the first back belt portion 112 with respect to the guidelines.

Figure 5:
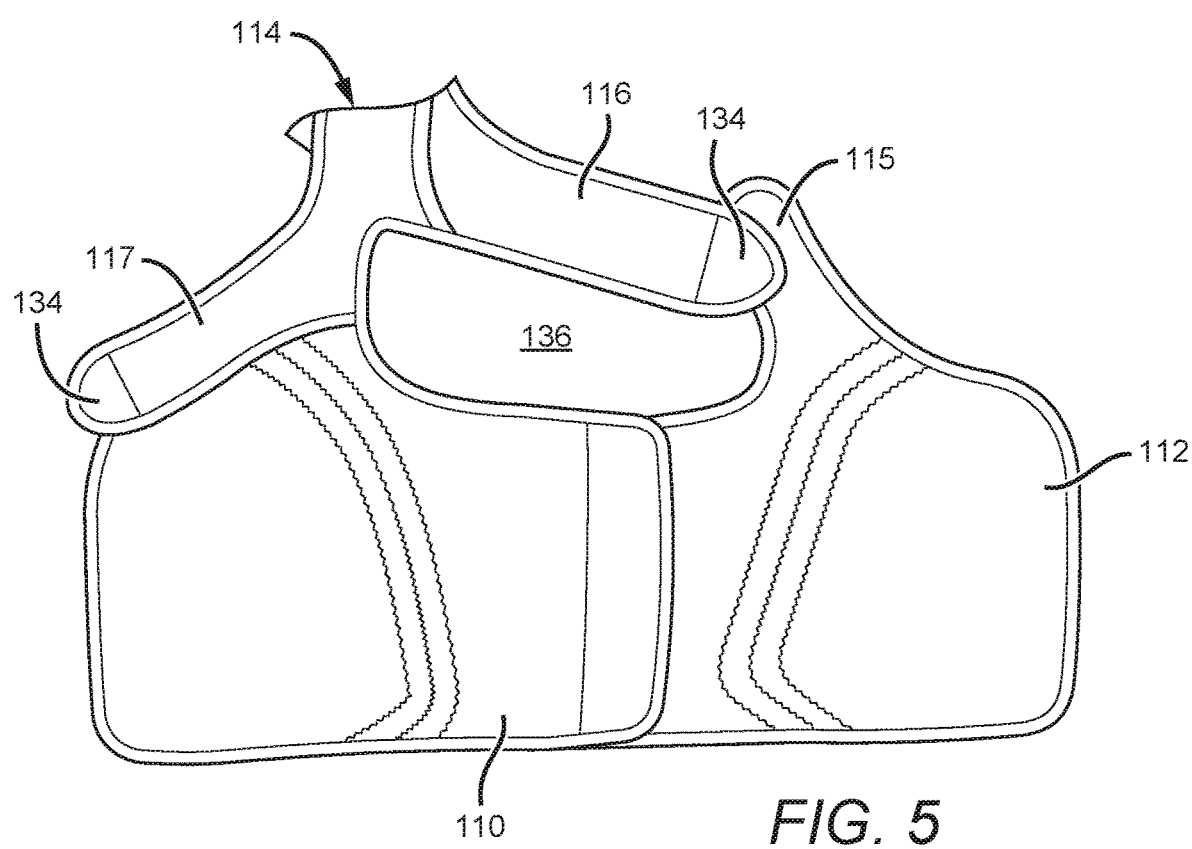
FIG. 5 is another partial view of the torso portion according to an aspect of the disclosure.
Figures 20, 21:
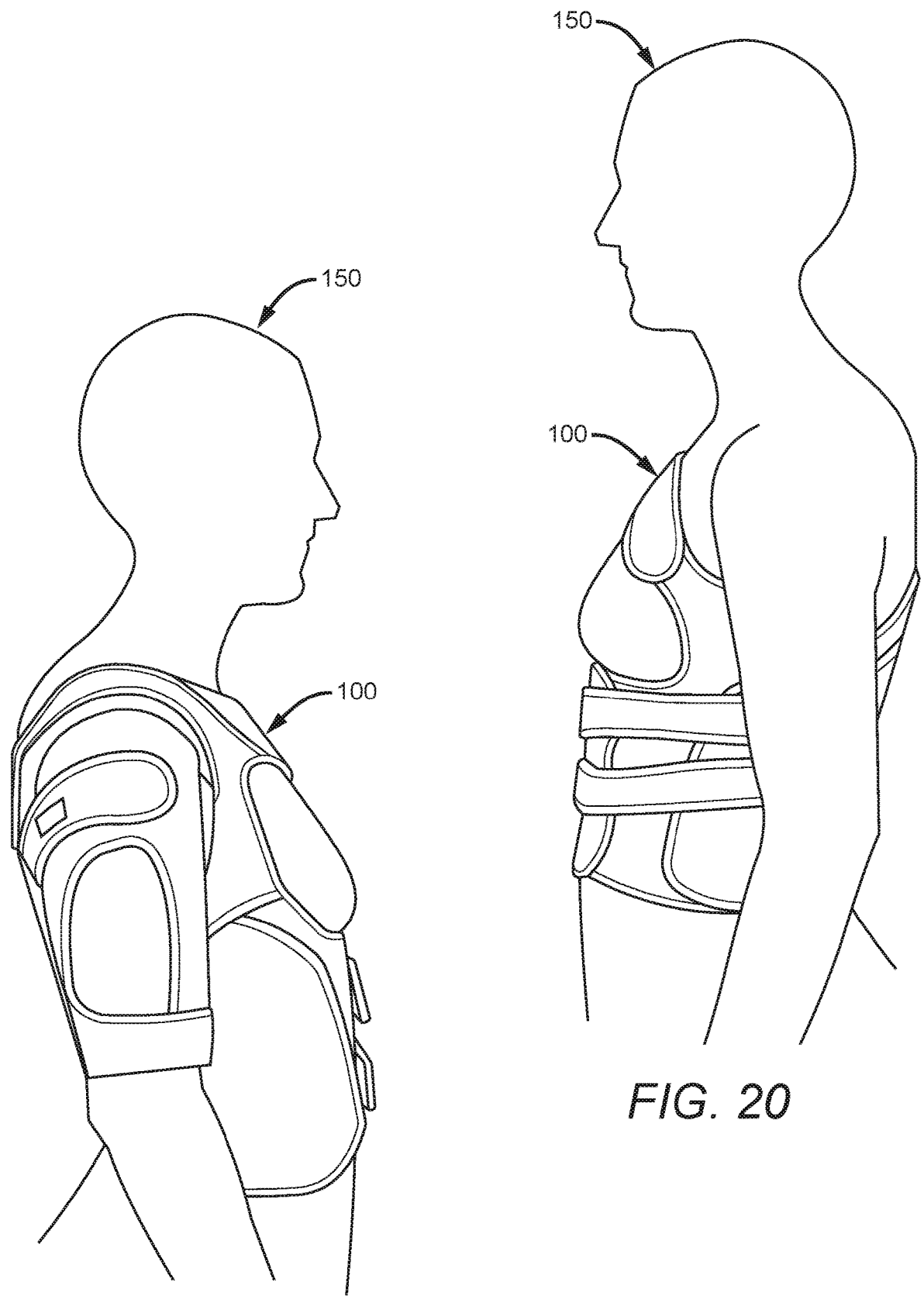
FIG. 20 is a side view of the user utilizing the orthopedic device of FIG. 19.
FIG. 21 is another side view of the user utilizing the orthopedic device of FIG. 19.
Figure 23:
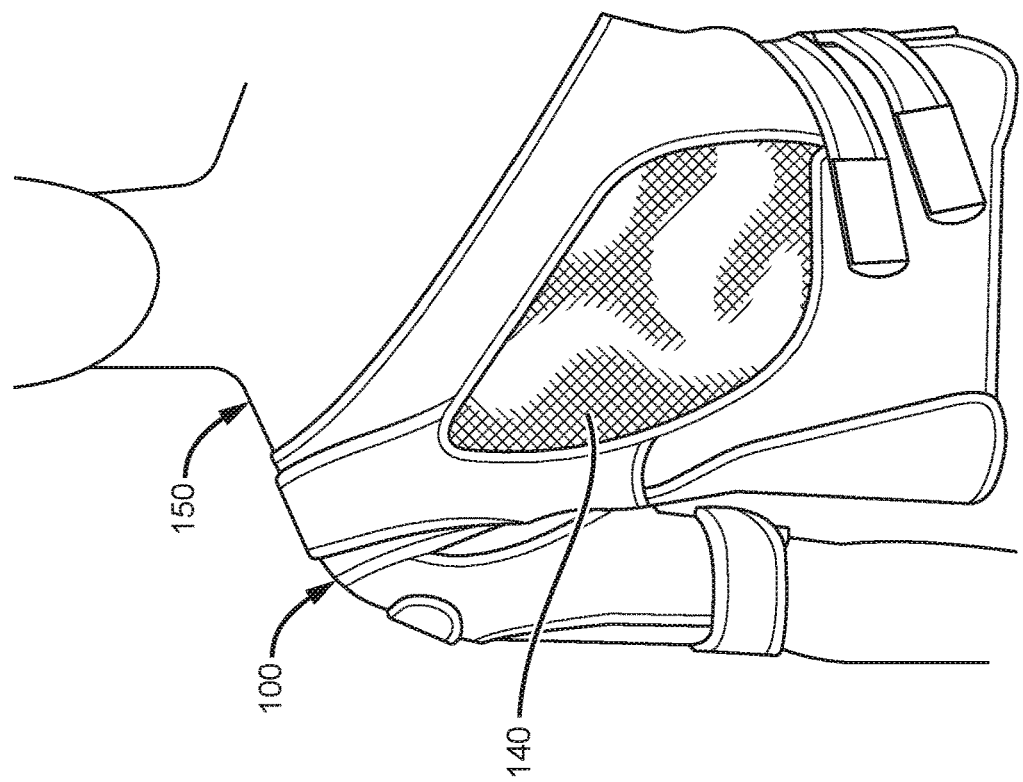
FIG. 23 is a perspective view of a user utilizing an orthopedic device according to an aspect of the disclosure.
Figure 22:
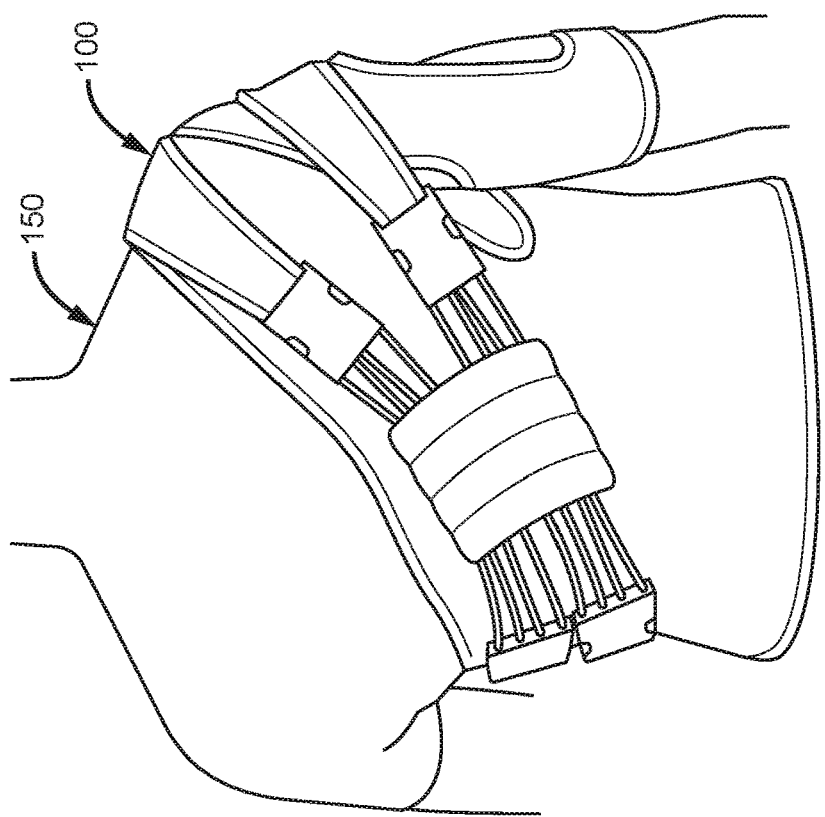
FIG. 22 is a rear view of the user utilizing the orthopedic device of FIG. 19.

FIG. 5 shows an aspect of the front belt portion 110 coupled to the first back belt portion 112. The mounting region 134 of the front belt portion 110 is removably coupled to the outer surface of the first back belt portion 112. The mounting region 134 of the front belt portion 110 is on an interior surface of the front belt portion 110. The plurality of hooks of the mounting region 134 of the front belt portion 110 securely fasten the front belt portion 110 to the first back belt portion 112. The at least one shoulder band 116 can then be coupled to the mount region 115 of the first back belt portion 112. The at least one shoulder band 116 also comprises a mounting region 134 that can comprise a plurality of hooks (not shown), similar to the mounting region 134 of the front belt portion 110. Coupling the front belt portion 110 to the first back belt portion 112 and the at least one shoulder band 116 to the first back belt portion 112, forms an opening 136. The opening 136 can be substantially aligned with the chest region of the user. In some aspects, the opening 136 can accommodate for various sized and shaped chest regions of users, for example breast region of female and/or male users, as shown in FIG. 20 or 21. The opening 136 allows the chest region of the user to not be compressed or provide discomfort when utilizing the orthopedic device 100. In some aspects, the opening 136 can comprise a mesh 140 that can cover the chest region of users, as shown in FIG. 23.

FIG. 5 appears to disclose a front shoulder band portion 117 as being coupled to the front belt portion 110. However, the front shoulder band portion 117 is not intended to be coupled to the front belt portion 110 as shown in FIG. 5. The front shoulder band portion 117 is configured to be coupled to at least the second back belt portion 112, and will be further discussed below. The aspect of FIG. 5 shows the front belt portion 110 and the first back belt portion 112 laid out in a flat arrangement, for ease of illustration.

Figure 6:
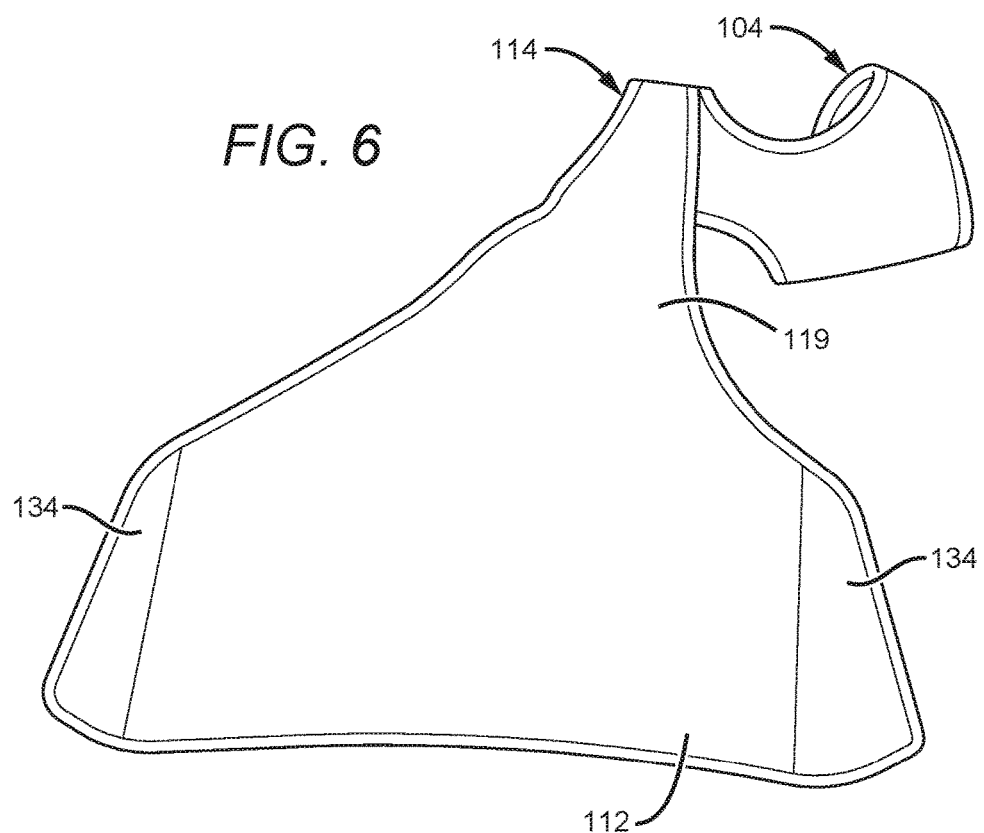
FIG. 6 is another partial view of the torso portion according to an aspect of the disclosure.

FIG. 6 shows the second back belt portion 112 laid out in a flat arrangement. The second back belt portion 112 comprises a first mounting region 134 and a second mounting region 134 opposite the first mounting region 134. The first mounting region 134 of the second back belt portion 112 is configured to receive the first back belt portion 112. The second mounting region 134 of the second back belt portion 112 is configured to receive the front belt portion 110. FIG. 6 also shows a rear view of the shoulder portion 114 of the torso portion 102. The shoulder portion 114 comprises a back shoulder band portion 119 that extends between the belt portion 108 and the at least one front shoulder band portion 116. The back shoulder band portion 119 is fixedly attached to the at least one front shoulder band portion 116. FIG. 6 also shows the upper arm portion 104. The upper arm portion 104 is coupled to the torso portion 102 proximate the shoulder portion 114. In some aspects, the upper arm portion 104 is coupled to the shoulder portion 114 proximate to where the back shoulder band portion 119 is fixedly attached to the at least one front shoulder band portion 116. However, the upper arm portion 104 can be coupled to the shoulder portion 114 in many different regions and is not intended to be limited to the where the back shoulder band portion 119 is fixedly attached to the at least one front shoulder band portion 116. In some aspects, the region wherein the back shoulder band portion 119 is fixedly attached to the at least one front shoulder band portion 116 is configured to substantially align with the shoulder of the user. However, in some aspects, the region wherein the back shoulder band portion 119 is fixedly attached to the at least one front shoulder band portion 116 does not necessarily align with the shoulder of the user and can be in front or behind the shoulder of the user.

Figure 7:
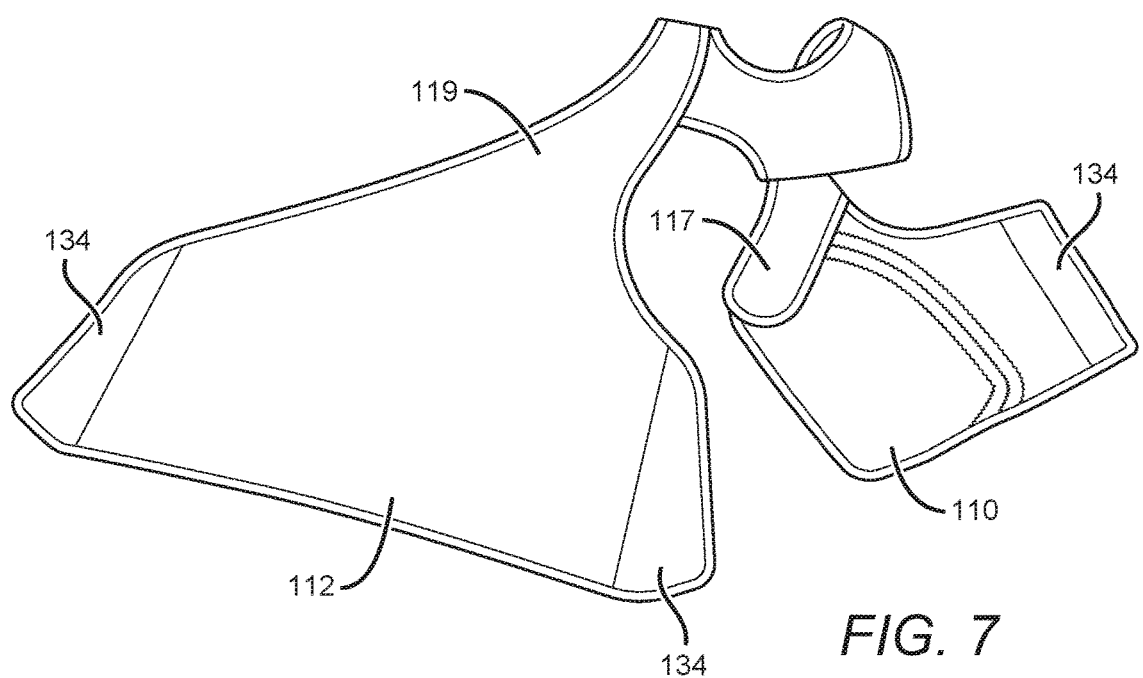
FIG. 7 is another partial view of the torso portion according to an aspect of the disclosure.
Figure 8:
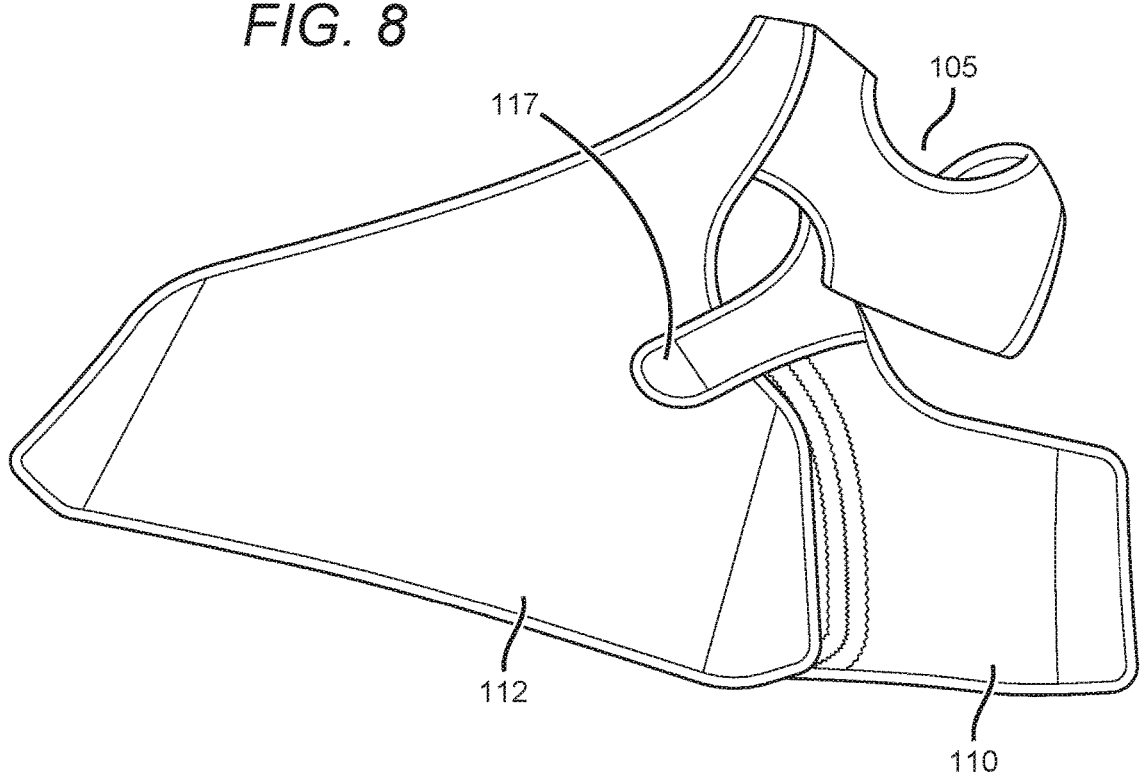
FIG. 8 is another partial view of the torso portion according to an aspect of the disclosure.

FIGS. 7 and 8 show an aspect of the second back belt portion 112 coupled to the front belt portion 110. The second mounting region 134 of the second back belt portion 112 is configured to be coupled to the front belt portion 110. The mounting regions 134 of the second back belt portion 112 are similar to the mounting regions 134 discussed above. As such, the second mounting region 134 of the second back belt portion 112 is coupled to the exterior surface of the front belt portion 110, such that the second back belt portion 112 is coupled to the front belt portion 110. The second mounting region 134 of the second back belt portion 112 can be coupled to the front belt portion 110 with respect to the guidelines 132. However, as discussed above, the guidelines 132 are intended as a reference guide, but it is not required that the second back belt portion 112 be coupled to the front belt portion 110 with respect to the guidelines 132. The exterior surface of the front belt portion 110 comprises a plurality of loops such that the second mounting region 134 of the second back belt portion 112 can be received at any part of the exterior surface of the front belt portion 110.

With reference to FIG. 8, the coupling of the second back belt portion 112 to the front belt portion 110 allows the front shoulder band portion 117 to be properly positioned. As discussed above, the front shoulder band portion 117 is configured to be coupled to at least the second back belt portion 112. The front shoulder band portion 117 extends from the shoulder portion 114 towards the second back belt portion 112. The front shoulder band portion 117 comprises a mounting region 134, similarly as discussed above, that is configured to be received by the outer surface of the second back belt portion 112. The outer surface of the second back belt portion 112 comprises a plurality of loops to receive the plurality of hooks of the mounting region of the front shoulder band portion 117. In some aspects, the front shoulder band portion 117 can be coupled to the back shoulder band portion 119. The back shoulder band portion 119 has a plurality of loops on its exterior surface, similar to the second back belt portion 112. At least one advantage of the disclosure is that the front shoulder band portion 117 is configured to adjust the fitment of the orthopedic device on the user. For example, the front shoulder band portion 117 can be coupled to either the back shoulder band portion 119 or the second back belt portion 112 in order to adjust the fit of the orthopedic device 100. Adjusting the placement of the front shoulder band portion 117 allows the orthopedic device to be adjusted due to different body types and/or to increase/decrease the compression to part of the torso of the user when utilizing the orthopedic device 100.

Figure 9:
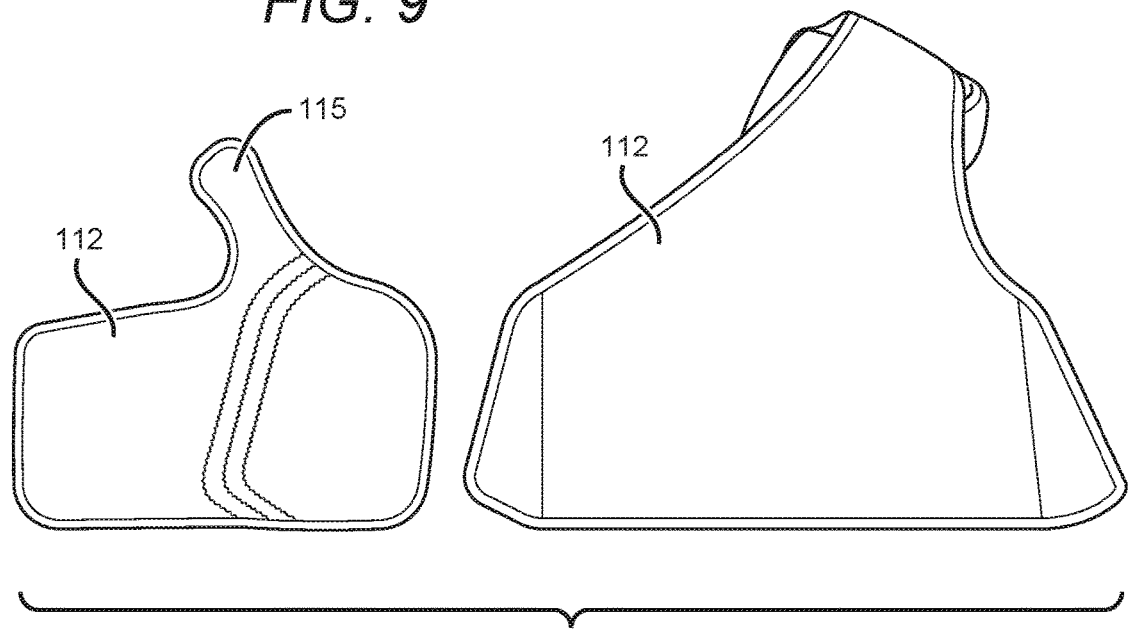
FIG. 9 is another partial view of the torso portion according to an aspect of the disclosure.

FIGS. 9 and 10 show an aspect of the first back belt portion 112 coupled to the second back belt portion 112. The first mounting region 134 of the second back belt portion 112 is configured to be received by the first back belt portion 112. The first mounting region 134 of the second back belt portion 112 is coupled to the exterior surface of the first back belt portion 112, such that the second back belt portion 112 is coupled to the first back belt portion 112. The first mounting region 134 of the second back belt portion 112 can be coupled to the first back belt portion 112 with respect to the guidelines 132. However, as discussed above, the guidelines 132 are intended as a reference guide, and it is not required that the second back belt portion 112 be coupled to the first back belt portion 112 with respect to the guidelines 132. The exterior surface of the first back belt portion 112 comprises a plurality of loops such that the first mounting region 134 of the second back belt portion 112 can be received at any part of the exterior surface of the first back belt portion 112. The coupling of the front belt portion 110 and the first and second back belt portions 112, 112 form the belt portion 108, as shown in FIG. 11, such that the belt portion 108 is adapted to secure the orthopedic device to the torso of the user.

At least one advantage of the disclosure is that the front belt portion 110 and the first and second back belt portions 112, 112 are adjustable such that the belt portion 108 can accommodate various different users. The size of the belt portion 108 can be increased or decreased as desired by the user, which allows the orthopedic device 100 to be a universal orthopedic device 100. Conventional orthopedic devices come in limited size ranges and may not accommodate an array of different sized users, whereas the size of the orthopedic device 100 can be adjusted to accommodate various sized users. In some aspects, a user with a smaller than average torso could remove the first back belt portion 112 and only use the front belt portion 110 and the second back belt portion 112, wherein the second back belt portion 112 is coupled to the front belt portion 110. The front belt portion 110 can be coupled to the exterior surface of the second back belt portion 112, or the second back belt portion 112 can be coupled to the exterior surface of the front belt portion 110. In either configuration, the at least one shoulder band 116 can be coupled to the second back belt portion 112. In yet some aspects, a user with a larger than average torso could add another first back belt portion 112 to further extend the size of the belt portion 108.

The torso portion 102 can further comprise a shoulder portion 114 adapted to be removably coupled to the belt portion 108. The shoulder portion 114 comprises at least one shoulder band 116 that extends towards the first back belt portion 112, such that the shoulder portion 114 is removably coupled to the belt portion 108. The shoulder portion 114 comprises at least one shoulder band 116 that extends towards the first back belt portion 112 to removably couple the shoulder portion 114 to part of the first back belt portion 112. In some aspects, the first back belt portion 112 can comprise a mount region 115 to receive the at least one shoulder band 116 to removably couple the at least one shoulder band 116 to part of the first back belt portion 112. In some aspects, the at least one shoulder band 116 can be removably coupled to any part of the exterior surface of the first back belt portion 112. In the aspect of FIGS. 1 and 2, the shoulder portion 114 comprises a first front shoulder band 116, a second front shoulder band 117, and a back shoulder band portion 119, wherein the first shoulder band 116 is removably coupled to the first back belt portion 112, and the second shoulder band 117 is removably coupled to the second back belt portion 112. The shoulder portion 114 can be configured in many different ways and is not intended to be limited to the aspects disclosed herein. In some aspects, the shoulder portion 114 can comprise more than two front shoulder bands or could comprise one front shoulder band. In some aspects, the shoulder portion 114 can comprise a plurality of back shoulder band portions 119. In some aspects, the second shoulder band 117 can be removably coupled to the back shoulder band portion 119. The positioning of the first and/or second shoulder bands 116, 117 on the respective back belt portions can be adjusted such that the way the orthopedic device 100 fits on the user can be customized. For example, the first and/or second shoulder bands 116, 117 can tighten or loosen the fit of the orthopedic device 100 by altering the coupling position on the respective back belt portions. The first and/or second shoulder bands 116, 117 also function to at least partially counter the force exerted by the support system 106. As will be discussed further below, the support system 106 exerts a force to at least the shoulder portion 114 to support the upper arm within the shoulder joint. The first and/or second shoulder bands 116, 117 being coupled to the respective back belt portions assist in anchoring the shoulder portion 114 such that the shoulder portion 114 is stabilized and does not substantially alter its position in response to the force exerted by the support system 106.

Figure 13:
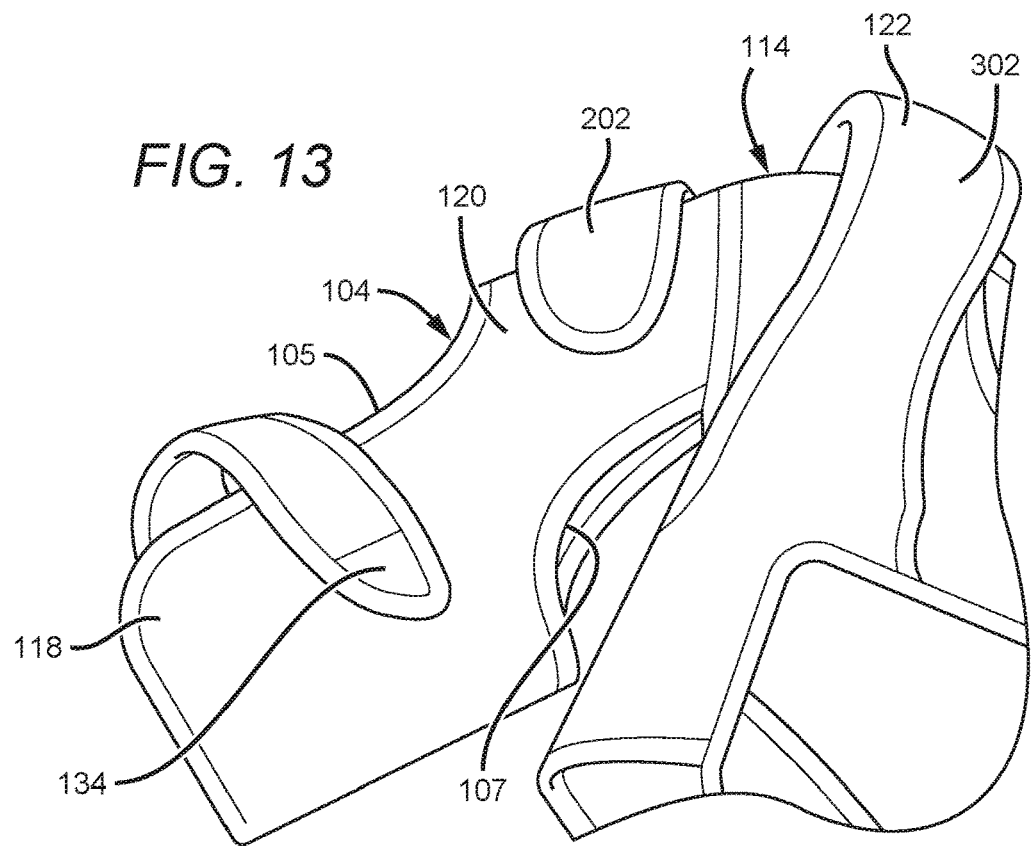
FIG. 13 is a partial view of the upper arm portion according to an aspect of the disclosure.
Figure 14:
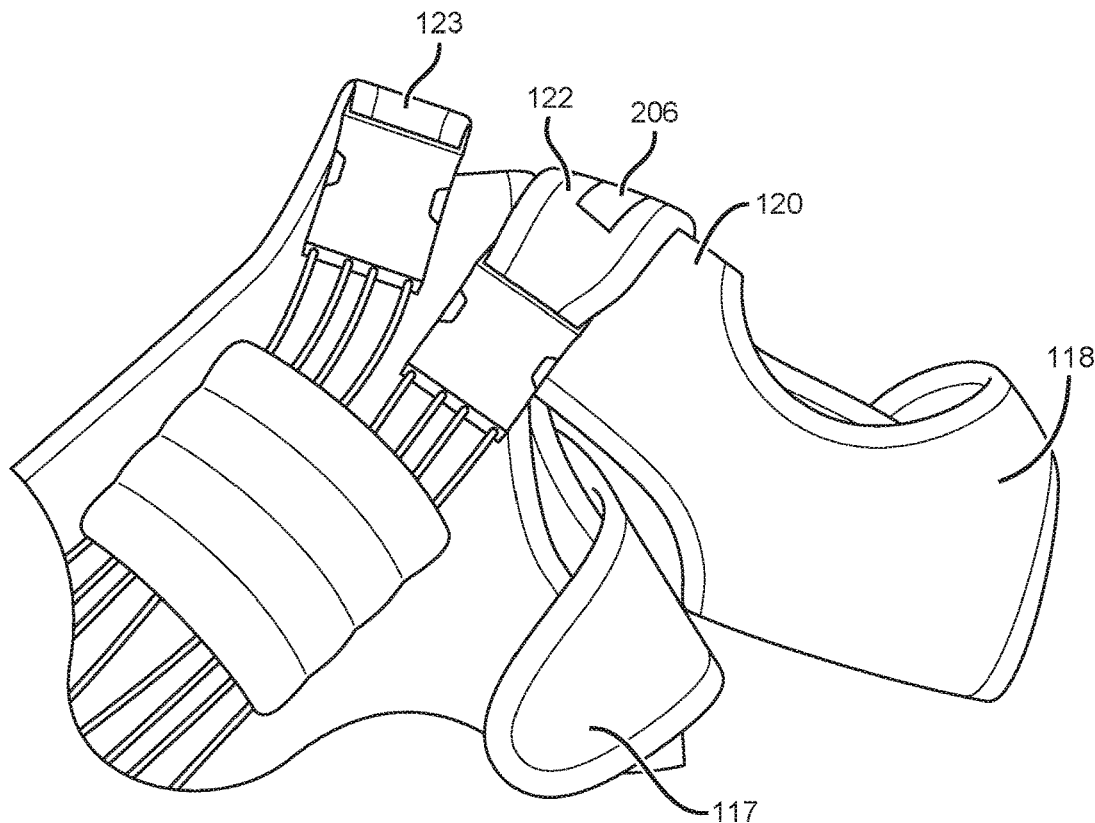
FIG. 14 is a partial rear view of the upper arm portion of FIG. 13.
Figure 15:
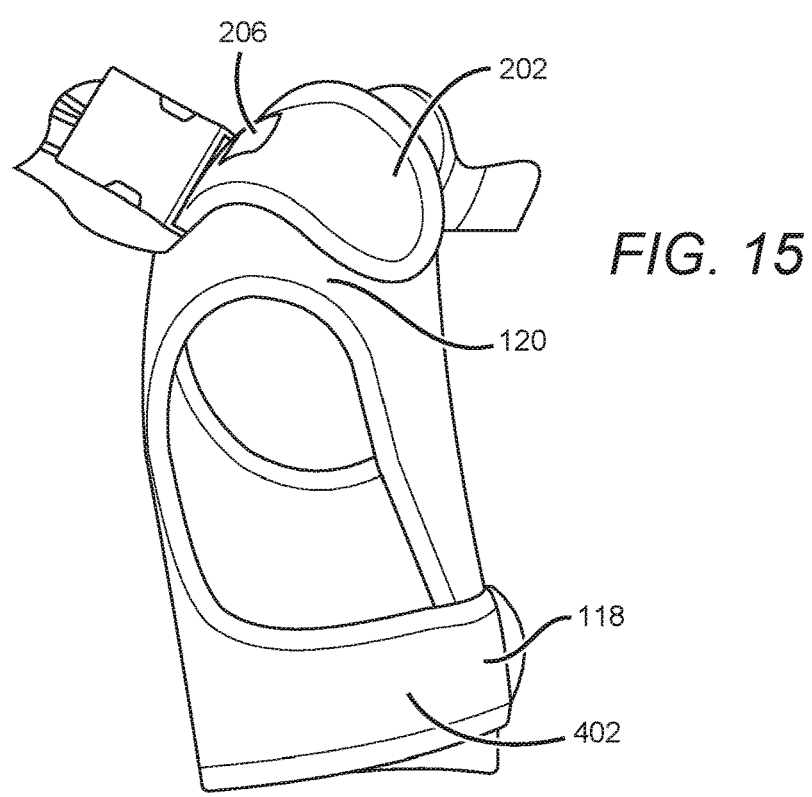
FIG. 15 is a side view of the upper arm portion of FIG. 13.
Figure 16:
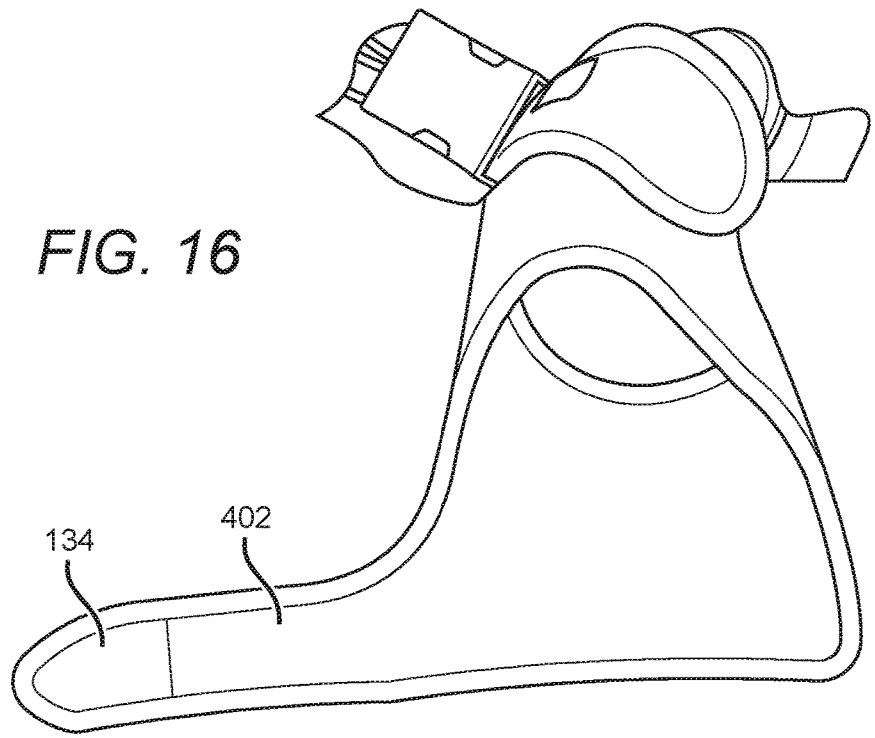
FIG. 16 is another side view of the upper arm portion of FIG. 13.

The upper arm portion 104, as shown in FIG. 13, is configured to receive the upper arm of the user. The upper arm portion 104 is coupled to the torso portion 102, proximate the shoulder portion 114. The upper arm portion 104 assists in stabilizing the upper arm while utilizing the orthopedic device 100. The upper arm portion 104 comprises an inner upper arm portion 120 and an outer upper arm portion 118, wherein the inner and outer upper arm portions can be removably coupled to each other. The inner upper arm portion 120 wraps around the underside of the upper arm, while the outer upper arm portion 118 wraps around the outer portion of the upper arm. The inner and outer upper arm portions 120, 118 substantially conform to the upper arm and wrap the upper arm within the upper arm portion 114. The upper arm portion 114 is adapted to apply a compression force onto the upper arm. In one aspect, as shown in FIGS. 13, 15, and 16, the outer upper arm portion 118 comprises at least one extension 402 that is configured to extend around the upper arm towards an opposing outer upper arm portion in order to secure the upper arm within the upper arm portion 104. The upper arm portion 104 can be configured in many different configurations and is not intended to be limited to the aspects disclosed herein. In some aspects, the upper arm portion 104 can comprise an inner upper arm portion 120 having at least one extension and an outer upper arm portion 118 having at least one extension in order to couple the inner and outer upper arm portions. The upper arm portion 104 is adjustable in order to accommodate differently sized upper arms. The upper arm portion 104, when wrapped around the upper arm, provides a compression force on the upper arm, and such force can be increased and/or decreased by adjusting the inner and outer upper arm portions, by either loosening and/or tightening the inner and outer upper arm portions.

Figure 26:
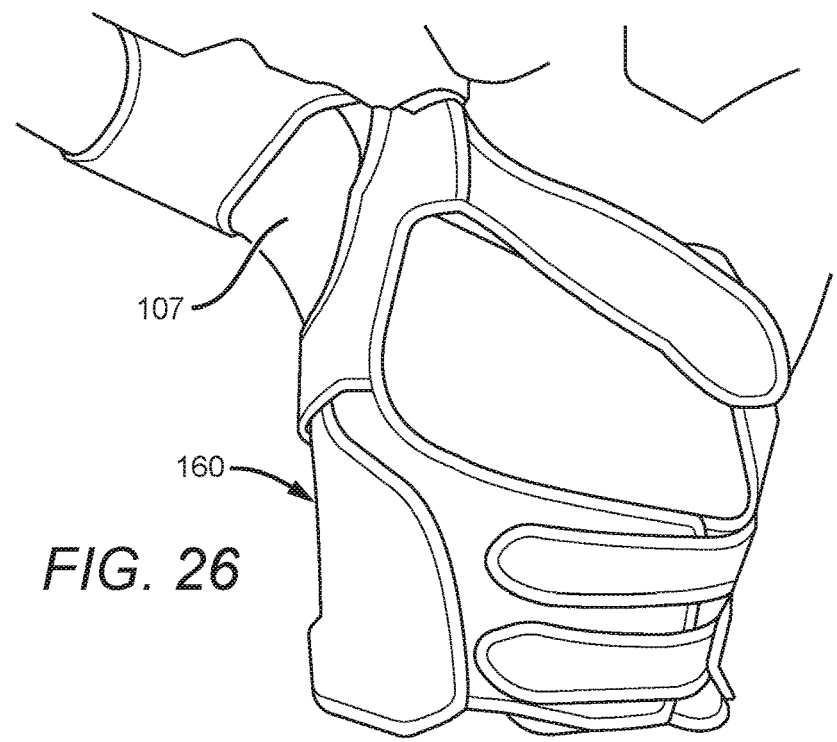
FIG. 26 is another perspective view of the user utilizing the orthopedic device of FIG. 24.

The upper arm portion 104 can further comprise at least one opening 105. The at least one opening 105 allows the upper arm portion 104 to move within the range of motion of the joint. As discussed above, when the upper arm portion 104 is wrapped around the upper arm of the user, the upper arm portion 104 is compressed about the upper arm, and the at least one opening 105 reduces and/or eliminates any constriction of movement that may be present due to the upper arm portion 104 compressing the upper arm. In the aspects of FIG. 13, the upper arm portion 104 comprises two openings, a first opening 105 on an outer arm region and a second opening 107 on an under arm region. FIG. 26 illustrates an aspect of the motion provided for abduction with compression about the upper arm of the user. The disclosure is not intended to be limited to the aspects disclosed herein. In some aspects, the upper arm portion 104 can comprise any number of openings and is not intended to be limited to two openings. The upper arm portion 104 can comprise one or more openings such that the one or more openings allows the upper arm portion 104 to move within the range of motion of the joint.

The support system 106 is adapted to support the upper arm within the shoulder joint while allowing a substantial full range of upper arm motion within the joint. In some aspects, the support system 106 comprises at least one strap 122 removably coupled to the upper arm portion 104. The at least one strap 122 is configured to mimic at least part of the muscular system structure and function of the muscles that are used during the range of motion of the shoulder joint, such as but not limited to the rotator cuff. In some aspects, the at least one strap 122 is removably coupled to the upper arm portion 104 at one end and removably coupled to at least one of the back belt portions 112 of the belt portion 108 at an opposing end. The at least one strap can be positioned so as to support the external rotator muscles on the shoulder. The at least one strap is configured to recreate muscles on the outside of the body of the user to improve natural movement of the joint. The strap being removably coupled allows the strap to be adjusted, which could increase and/or decrease the support provided to the upper arm within the joint. The at least one strap can be configured in a plurality of arrangements to augment the body's natural musculature and thereby facilitate biomechanical stability and appropriately stimulate the unconscious perception of movement i.e., proprioception, and spatial orientation arising from stimuli within the body itself. In some aspects, at least one strap is coupled to the shoulder portion 114 and is removably coupled to the first back belt portion 112 of the belt portion 108, which allows the orthopedic device 100 to be further adjusted for upper arm fitment by adjusting the placement of where the at least one strap is removably coupled to the first back belt portion 112 of the belt portion 108. Positioning the at least one strap further along the first back belt portion 112 of the belt portion 108 increases the support the at least one strap provides to the joint. The at least one strap exerts a pulling force onto at least the shoulder portion 114 such that the shoulder of the user is pulled back. The pulling force stabilizes the upper arm within the shoulder joint and supports at least some of the muscles of the rotator cuff, such as but not limited to the supraspinatus, infraspinatus, and/or the teres minor muscles. This support assists in stabilizing the upper arm within the shoulder joint during the range of motion and promotes proper alignment for maximal stable rotation. The at least one strap is positioned so as to apply a compression force proximate the joint and/or muscles proximate the joint. This compression force assists in properly aligning the joint during the range of motion, such that the upper arm and/or joint does not substantially deviate from the proper alignment.

The support system can be configured in many different ways and is not intended to be limited to the aspects disclosed herein. In some aspects, the support system 106 comprises at least one resistance band 124 and at least one strap 122, wherein the at least one strap 122 is configured to receive the at least one resistance band 124. The at least one strap 122 can be removably coupled to part of the torso portion 102, part of the upper arm portion 104, and/or a combination thereof, such that the orthopedic device 100 provides support to the shoulder joint. The at least one resistance band 124 and at least one strap 122, are configured in a similar manner as discussed above such that the resistance band and strap provide support to the joint while allowing a substantial full range of motion of the upper arm within the joint. In some aspects, the at least one resistance band and strap are also configured to provide resistance to at least the joint. The resistance provided to the joint allows the joint to be exercised such that the surrounding muscles can be strengthened and/or rehabilitated during use of the orthopedic device 100. The resistance band and strap are configured to be adjustable, such that the support provided by the resistance band and strap can be increased and/or decreased. In some aspects, the strap 122 can be removably coupled to the upper arm portion 104 and removably coupled to the first back belt portion 112 of the belt portion 108. The placement of the strap 122 at either the upper arm portion 104 and/or the first back belt portion 112 could adjust the pressure applied by the strap 122 and resistance band 124 to the joint. The placement of the strap 122 is configured to adjust the resistance provided by the resistance band 124 onto the joint. In some aspects, the support system 106 comprises a strap 123 coupled to the shoulder portion 114 and removably coupled to the first back belt portion 112 of the belt portion 108, wherein at least one resistance band 124 is received by opposing ends of the strap 123. The support provided by the strap 123 coupled to the shoulder portion 114 can be adjusted by altering where the strap 123 is removably coupled to the first back belt portion 112 of the belt portion 108. The support system 106 can be configured in many different configurations and is not intended to be limited to the aspects disclosed herein.

Figure 12:
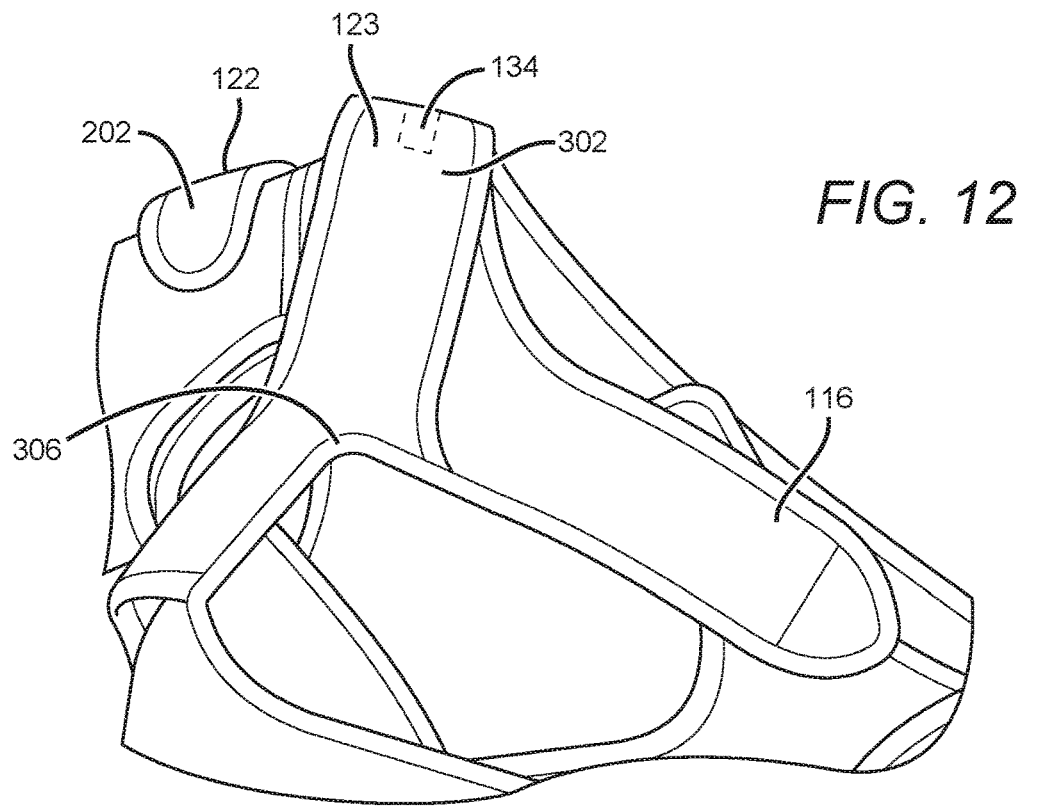
FIG. 12 is a partial view of the shoulder portion according to an aspect of the disclosure.
Figure 18:
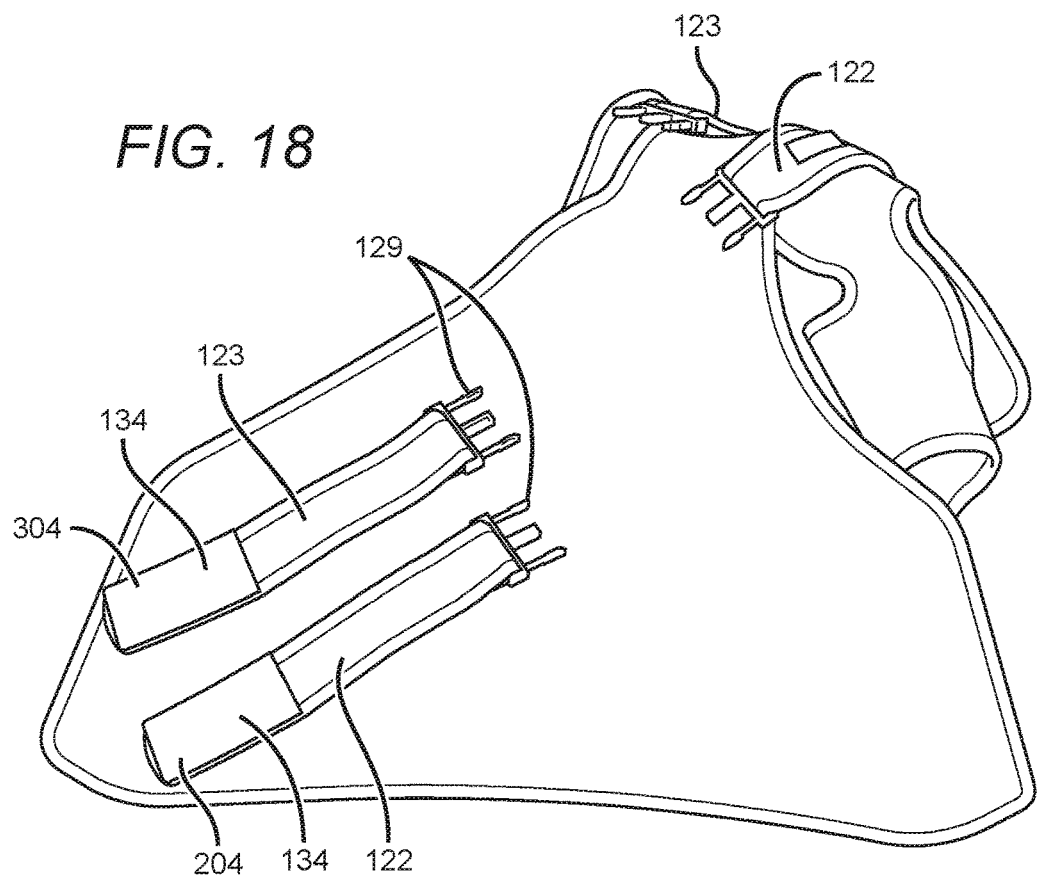
FIG. 18 is another partial view of a support system according to an aspect of the disclosure.
Figure 19:
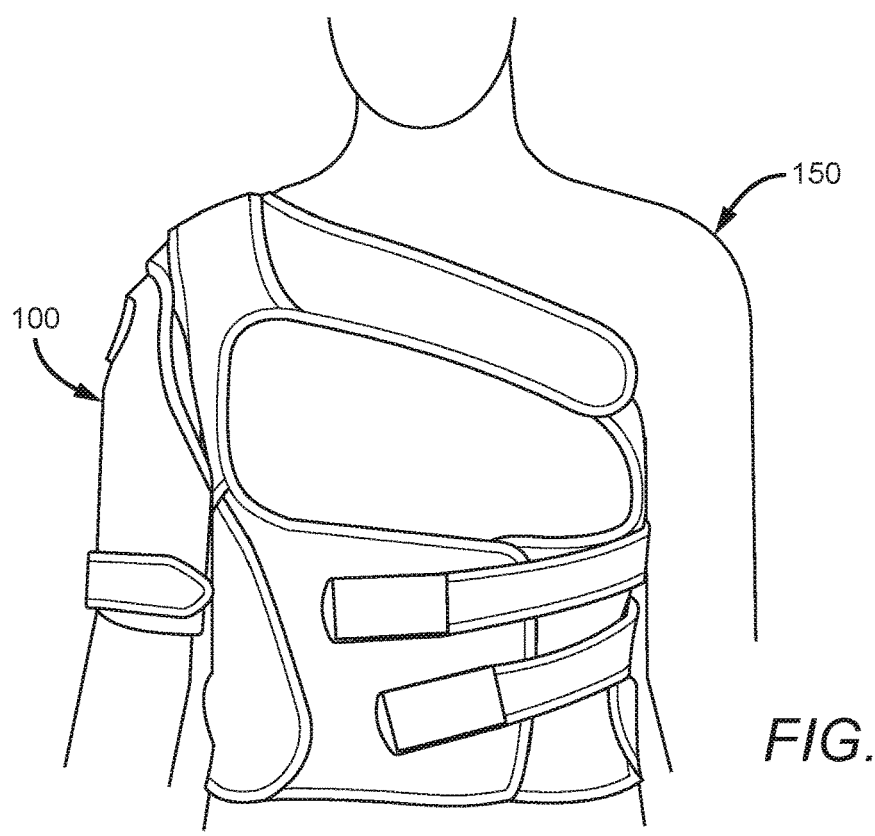
FIG. 19 is a perspective view of a user utilizing an orthopedic device according to an aspect of the disclosure.

In some aspects, the support system 106, as shown in FIGS. 1 and 2, comprises a first strap 122 having a first end 202 and a second end 204, wherein the first end 202 is coupled to part of the upper arm portion 104, and the second end 204 is coupled to part of the torso portion 102. The first strap 122 is configured to extend between the upper arm portion 104 and the torso portion 102 along a rear region of the orthopedic device 100. The first end 202 of the first strap 122 is attached to the upper arm portion 104, such that the upper arm portion 104 counters the force exerted by the first strap 122. The upper arm portion 104 is anchored due, in part, to the inner and outer upper arm portions 120, 118 securing the orthopedic device 100 to the upper arm. The first end 202 can be attached to the upper arm portion 104 at many different locations and is not intended to be limited to the aspect disclosed herein. In some aspects, as shown in FIGS. 12, 13, and 15, the first end 202 is attached to the inner upper arm portion 120, such that the first strap 122 extends over the inner upper arm portion 120 and is proximate the second opening 107. The first end 202 extending over the inner upper arm portion 120 places the first end 202 in an anterior shoulder position, such that the force exerted by the first strap 122 acts to pull the upper arm and/or the shoulder back to provide support to the upper arm within the shoulder joint. In some aspects, the first end 202 can be coupled at more than one location of the inner upper arm portion 120. For example, in the aspect of FIG. 15, the first end is further coupled to the inner upper arm portion 120 at a mounting region 206. The mounting region 206 assist in the coupling of the first end 202 to the upper arm portion 104. The mounting region 206 can comprise a plurality of hooks such that the mounting region 206 is removably coupled to the inner upper arm portion 120, while in some aspects, the mounting region 206 is fixedly attached to the inner upper arm portion 120. The second end 204 comprises a mounting region 134 comprising a plurality of hooks, such that the second end 204 can be removably coupled to part of the torso portion 102. As shown in FIG. 18, the second end 204 can be removably coupled to the exterior surface of the second back belt portion 112. However, the second end 204 can be mounted to many different portions of the torso portion 102 and is not intended to be limited to the second back belt portion 112. The second end 204 can be removably coupled to any one of the first back belt portion 112 or the front belt portion 110. The front belt portion 110 and the back belt portions 112 have a plurality of loops on their exterior surfaces which allows the mounting region 134 of the second end 204 to removably couple the first strap 122 to any part of the belt portion 108 and/or torso portion 102.

The support system 106 further comprises a second strap 123 having a first end 302 and a second end 304, wherein the first end 302 is coupled to part of the shoulder portion 114, and the second end 304 is coupled to part of the torso portion 102. The second strap 123 is configured to extend between the shoulder portion 114 and the torso portion 102 along the rear region of the orthopedic device 100, similarly as the first strap 122. The first end 302 of the second strap 123 is attached to the shoulder portion 114 proximate the first shoulder band 116 and the second shoulder band 117, such that the shoulder portion 114 counters the force exerted by the second strap 123. In some aspects, as shown in FIG. 12, the first end 302 is attached to the shoulder portion 114 at a shoulder anchor section 306. The shoulder anchor section 306 is interposed between the first and second shoulder bands 116, 117. The shoulder anchor section 306 is along part of a perimeter of the opening 136. However, the shoulder anchor section 306 is not intended to be limited to the aspects disclosed herein. In some aspects, the shoulder anchor section can be anywhere along the shoulder portion 114 and does not have to be limited to being interposed between the first and second should bands 116, 117 and/or along part of the perimeter of the opening 136. In some aspects, the shoulder anchor section 306 can be separate from the perimeter of the opening 136. The first end 302 of the second strap 123 can further comprise a mounting region 134 comprising a plurality of hooks, wherein the mounting region 134 of the first end 302 can be removably coupled to the shoulder portion 114. The mounting region 134 provides additional support to the first end 302. In some aspects, the mounting region 134 of the first end 302 allows the positioning of the second strap 123 to be at least partially adjusted, such that the alignment of the second strap 123 can be altered. The shoulder portion 114 is anchored due, in part, to the first and second shoulder bands 116, 117 being coupled to the respective back belt portions 112. The plurality of belt portions 110, 112 that are coupled together to form the belt portion 108 secure the orthopedic device 100 to the torso of the user, such that when the belt portion 108 is secured to the torso of the user the belt portion 108 functions to anchor the shoulder portion 114 by way of the first and second shoulder bands 116, 117. The belt portion 108 when secured to the torso does not substantially alter its position which thereby resists the force exerted by the second strap 123 onto the shoulder portion 114. The force exerted by the second strap 123 provides support to the muscles surrounding the shoulder to substantially maintain joint alignment throughout the upper arm range of motion. The second end 304 is similar to the second end 204 and comprises a mounting region 134 comprising a plurality of hooks, such that the second end 304 can be removably coupled to part of the torso portion 102. As shown in FIG. 18, the second end 304 can be removably coupled to the exterior surface of the second back belt portion 112. However, the second end 304 can be mounted to many different portions of the torso portion 102 and is not intended to be limited to the second back belt portion 112. The second end 304 can be removably coupled to any one of the first back belt portion 112 or the front belt portion 110. The front belt portion 110 and the back belt portions 112 have a plurality of loops on their exterior surfaces which allows the mounting region 134 of the second end 304 to removably couple the second strap 123 to any part of the belt portion 108 and/or torso portion 102.

Figure 17:
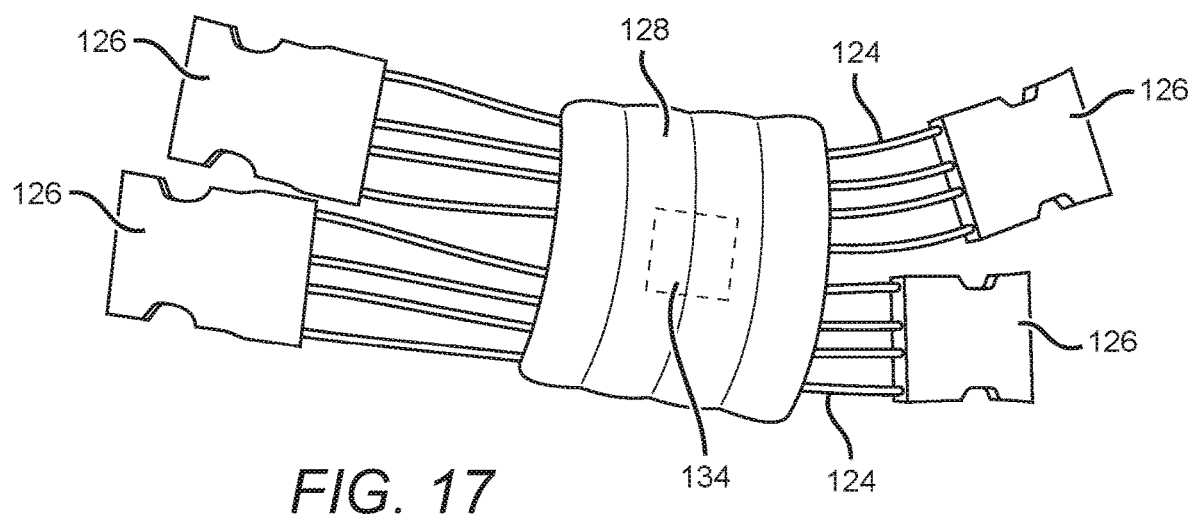
FIG. 17 is a partial view of a support system according to an aspect of the disclosure.

The support system 106 can further comprise at least one resistance band 124, wherein at least one first resistance band 124 is received by the first strap 122, and at least one second resistance band 124 is received by the second strap 123. In the aspect of FIG. 2, each of the first and second straps are configured to receive a plurality of resistance bands 124, wherein the first strap 122 receives a first plurality of resistance bands 124 and the second strap 123 receives a second plurality of resistance bands 124. The first and second plurality of resistance bands 124 are removably coupled to the respective first and second strap. With reference to FIGS. 17 and 18, the first and second plurality of resistance bands 124 comprise couplers 126 at opposing ends of the plurality of resistance bands. The first and second straps 122, 123 comprise tabs 129 adapted to engage the couplers 126, such that the tabs 129 are received by the couplers 126 to fasten the first and second straps to the respective plurality of resistance bands 124. The tabs 129 can be disengaged from the couplers 126 to release the resistance bands from the straps, such that the resistance bands are removably coupled to the respective straps. The straps and resistance bands can be removably coupled using many different coupling devices known in the art to removably couple two elements, such as but not limited to cliplocks, hook and loop systems, clasps, stops, and the like, and the disclosure is not intended to be limited to the couplers 126 and tabs 129 disclosed herein.

The resistance bands 124 extend between the couplers 126 of the first and seconds straps and provide the resistance and/or support to the joint. Extending the resistance bands increases the resistance provided to the joint, which allows the joint to be exercised in order to strengthen the muscles surrounding the joint. Strengthening the muscles helps to stabilize the joint, as well as promote proper joint alignment. Improper alignment of the joint can be caused by weak muscles that are used during the range of motion of the joint. The orthopedic device strengthens weak muscles to improve stability and alignment of the joint. The resistance bands can be extended by altering the position of the ends 204, 304 of the first and/or second straps 122, 123. The ends of the first and/or second straps can be adjusted by pulling the ends in a direction towards the front belt portion 110 and/or first back belt portion 112, such that the ends of the first and/or second straps can be coupled to the first back belt portion 112 or the front belt portion 110. This extends the resistance bands which thereby increases the force exerted onto either the upper arm portion 104 and/or the shoulder portion 114. The resistance can be increased by extending one or both of the straps 122, 123. Conversely, the resistance can be decreased by retracting the ends in an opposite direction from the front belt portion 110 and/or first back belt portion 112 towards the second back belt portion 112. Retracting the resistance bands reduces the force exerted onto either the upper arm portion 104 and/or the shoulder portion 114. As such, the force exerted by the support system 106 can be customized as desired, by adjusting one or both of the straps 122, 123.

The support system 106 can further comprise a resistance band housing 128, wherein each of the at least one resistance bands 124 is received by the resistance band housing 128. The resistance band housing 128 ensures that the at least one resistance bands 124 are properly aligned and do not become tangled, which could impact the effectiveness of the resistance bands. The resistance band housing 128 can comprise one or more channels (not shown), wherein each resistance band is received within a respective channel in order to maintain proper alignment of the at least one resistance bands. In some aspects, the resistance band housing 128 can comprise a mounting region 134, as shown in FIG. 17. The mounting region 134 of the resistance band housing 128 can comprise a plurality of hooks, such that the resistance band housing 128 can be removably coupled to the exterior surface of the torso portion 102. In some aspects, the mounting region 134 of the resistance band housing 128 can be removably coupled to the back shoulder band portion 119. In some aspects, the mounting region 134 of the resistance band housing 128 can be removably coupled to the second back belt portion 112. The resistance band housing 128 being removably coupled allows the resistance band housing 128 to substantially maintain the arrangement of the first and second straps, such that the force exerted by the first and/or second straps is substantially maintained.

At least one advantage of the disclosure is that the support system 106 is configured to assist the muscles surrounding the joint to facilitate proper alignment of the upper arm within the shoulder joint. The support system 106 exerts a force pulling the shoulder and/or the upper arm back to hold back the shoulder and/or upper arm in an anatomically correct position, i.e., to a position allowing maximal rotational stability. At least another advantage of the disclosure is that the support system 106 and/or the upper arm portion 104 can supply a compressive force to support anterior shoulder musculature. The orthopedic device 100 supports the muscles of the rotator cuff and allows the user to rehabilitate and/or strengthen injured and/or weakened muscles. Shoulder issues can arise due to instability of the shoulder as a result of over developed front muscles and under developed back muscles. As a result, the rotator cuff muscles can experience increased stress, especially in throwing motions, such as but not limited to a baseball throwing motion. The orthopedic device 100 allows users to strengthen under developed back muscles to stabilize the shoulder, and limit or reduce stress exerted onto the rotator cuff muscles during throwing motions.

Figure 27:
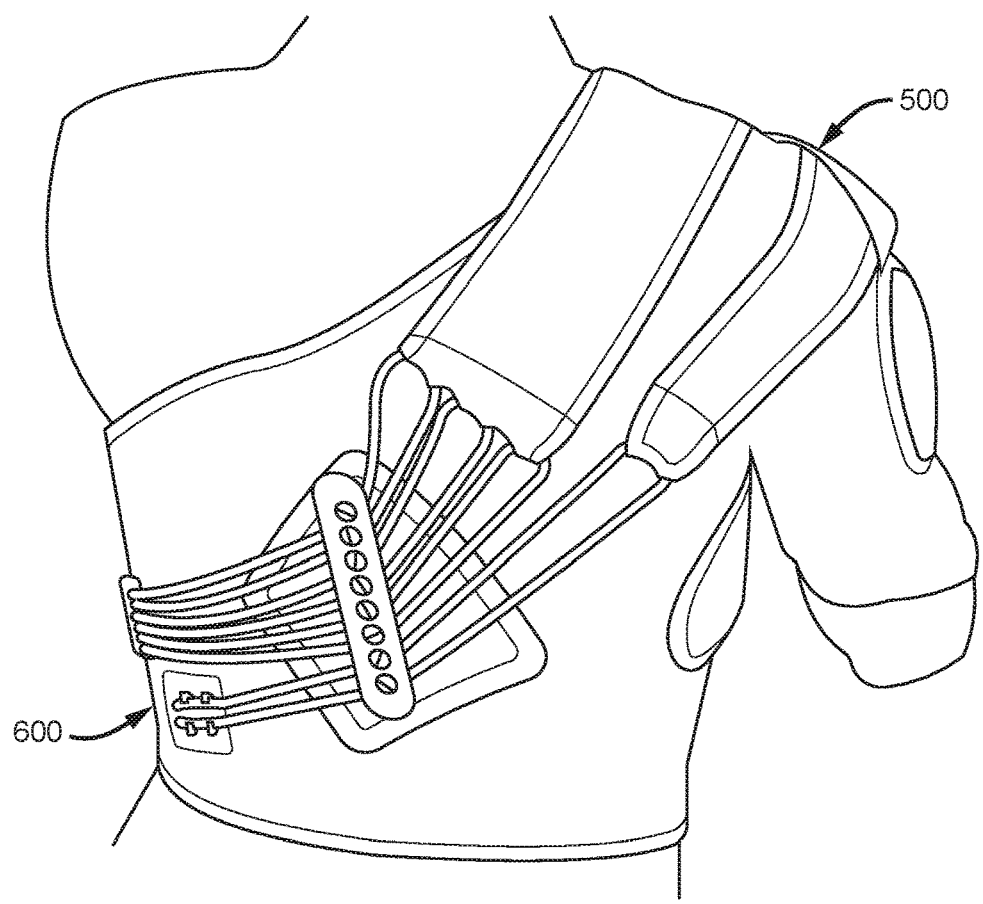
FIG. 27 is a rear view of a user utilizing an orthopedic device according to an aspect of the disclosure.

In the aspect of FIG. 2, the support system 106 comprise one resistance band housing that receives the at least one resistance bands. However, in other aspects, the support system can comprise more than one resistance band housing, and is not intended to be limited to the aspect disclosed herein. For example, in some aspects, the support system 106 can comprise a resistance band housing for each of the straps 122, 123, such that the at least one resistance bands of each strap are independently aligned. The respective resistance band housing can also removably couple the respective straps independently to maintain the arrangement of the straps. In some aspects, as shown in FIG. 27, the resistance band housing of a support system 600 can be affixed to the torso portion of the orthopedic device, while in other aspects the resistance band housing is not coupled to the orthopedic device.

At least one advantage of the disclosure is that the at least one resistance bands can be removably coupled to the straps, such that that at least one resistance bands can be replaced. This also allows the at least one resistance bands to be replaced in the event that the at least one resistance bands is damaged. For example, with reference to FIG. 17, the resistance bands can be detached from the straps 122, 123 by disengaging the coupler 126 from the tabs 129. This allows for replacement resistance bands to be coupled to the straps 122, 123. In some aspects, the resistance provided by the resistance bands can be further increased and/or decreased by replacing the existing at least one resistance bands with other resistance bands that provide a higher and/or lower resistance. For example, if a user has a shoulder injury that is to be exercised with minimal resistance, the resistance bands can be replaced with lower rated resistance bands to ensure that excessive resistance is not provided. In other aspects, a user could have sufficiently strengthened the muscles proximate the joint and desires to increase the resistance training provided by the orthopedic device, and in such instance, the resistance bands can be replaced with higher rated resistance bands.

FIGS. 19-23 show different views of the orthopedic device 100 being utilized on a user 150 in accordance with an aspect of the disclosure. The orthopedic device 100 allows the user 150 to have a substantially full range of upper arm motion.

Figure 25:
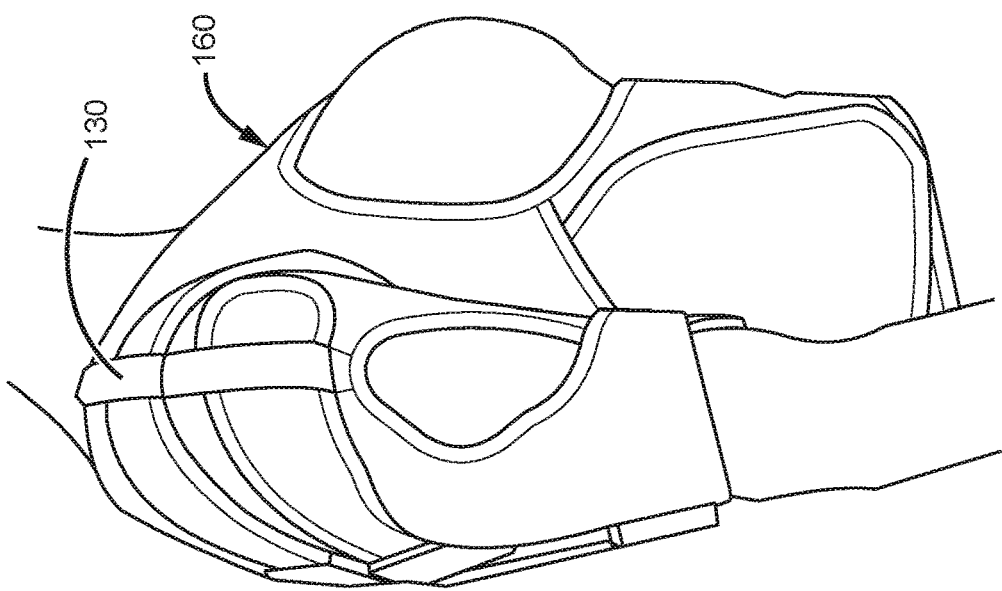
FIG. 25 is a side view of the user utilizing the orthopedic device of FIG. 24.
Figure 24:
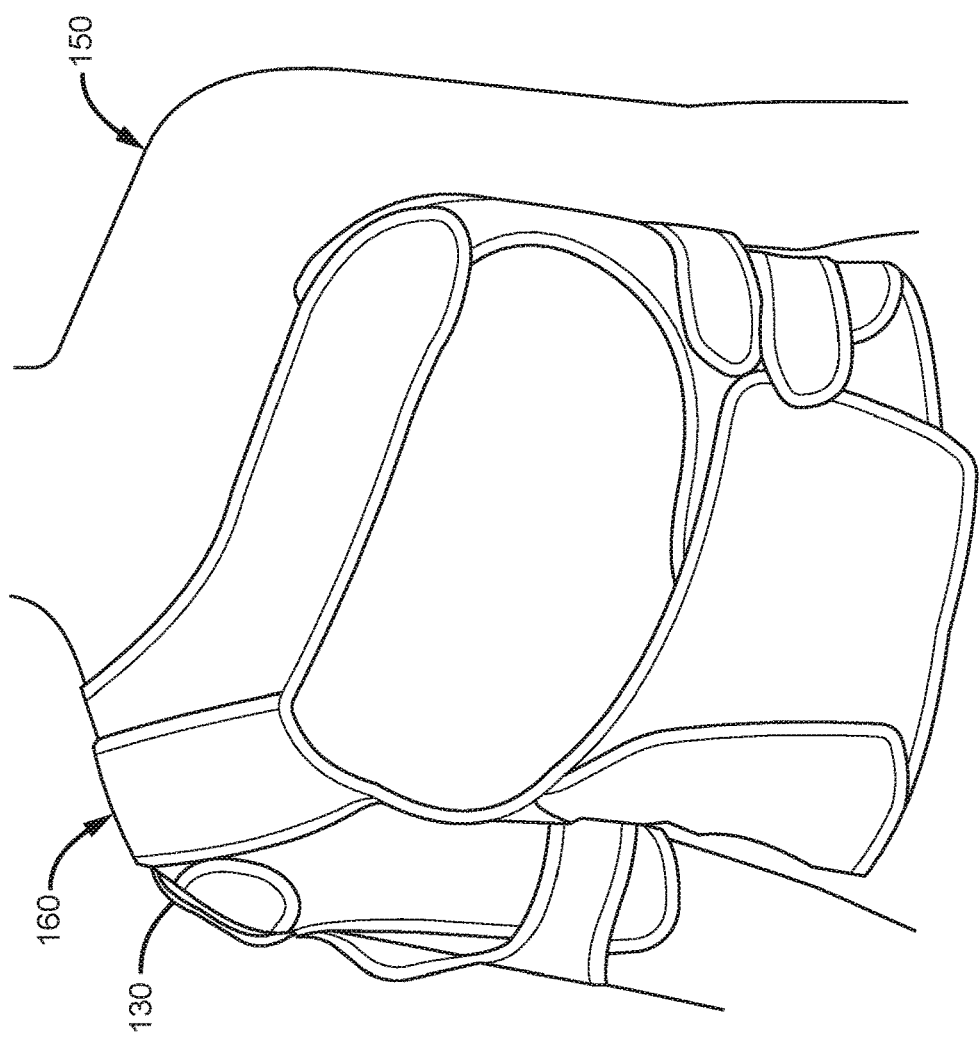
FIG. 24 is a perspective view of a user utilizing an orthopedic device according to an aspect of the disclosure.

With reference to FIGS. 24 and 25, an orthopedic device 160 comprises first and second straps that can be received by the strengthening member 130 on the upper arm portion and shoulder portion to properly align the first and second straps, such that the first and second straps are substantially aligned with at least some of the existing muscles proximate the joint. In some aspects, the orthopedic device 160 can comprise a strengthening member 130 on at least one of the upper arm portion and/or on the torso portion. In one aspect, the strengthening member is configured to maintain alignment of the upper arm portion and the shoulder portion, such that the upper arm portion is properly aligned during the range of motion of the joint. In some aspects, the strengthening member can be configured to cooperate with the support system to assist in proper alignment of the support system. With reference to FIG. and 25, the strengthening member 130 extends between the shoulder portion and the upper arm portion along the shoulder line of the user. At least one advantage of the disclosure is that the strengthening member can provide a visual indication to ensure that the orthopedic device is properly aligned with the joint. The visual indication provided by the strengthening member allows for the orthopedic device to be easily adjusted to ensure proper alignment. The strengthening member 130 is substantially aligned with the right shoulder line of the user. The disclosure is not intended to limit the strengthening member as being aligned with the shoulder line of the user. In other aspects, the strengthening member does not have to be aligned with the shoulder line of the user, and yet assists in aligning the upper arm portion and the torso portion. The strengthening member can be arranged in many different configurations while maintaining the alignment of the upper arm portion and the shoulder portion. In some aspects, the strengthening member can be on a front part of the orthopedic device, while in other aspects, the strengthening member can be on a back part of the orthopedic device. In yet other aspects, the orthopedic device can comprise one or more strengthening members on at least a front part of the orthopedic device, a back part of the orthopedic device, along the shoulder line of the user, and/or a combination thereof.

The support system 106 can be configured in many different ways and is not intended to be limited to the aspects disclosed herein. In some aspects, such as in FIG. 27, an orthopedic device 500 comprises a support system 600 wherein some of the at least one resistance bands can be coupled to the torso portion of the orthopedic device and received by a first strap, such that the first strap can be removably coupled to the upper arm portion. In the aspect of FIG. 27, the support system further comprises a second strap extending from the shoulder portion and removably coupled to the back portion of the belt portion. The second strap comprises at least one resistance band, such that the at least one resistance bands extend towards the back portion of the belt portion and are received by the second strap opposite the shoulder portion. In the aspect of FIG. 27, the at least one resistance bands are received by a casing comprising a plurality of pins, wherein the casing and plurality of pins align the at least one resistance bands and ensure that the at least one resistance bands do not become tangled with other resistance bands and maintain proper alignment. In some aspects, the at least one resistance bands can be received by a respective casing, wherein the at least one resistance bands are individually aligned. While in some aspects, a plurality of casings can receive one or more at least one resistance bands such that the one or more at least one resistance bands are aligned in groups by the plurality of casings.

The orthopedic device can be comprised of many different materials. In one aspect, the orthopedic device can be comprised of light weight breathable material, such as but not limited to neoprene, nylon, cotton, and/or the like, or a combination thereof. In some aspects, the orthopedic device can comprise a plurality of hook and loop regions on the torso portion in order for the front and back portions of the belt portion can be removably coupled. The orthopedic device can further comprise hook and loop regions on the shoulder portion and upper arm portion, such that the at least one strap can be removably coupled to the shoulder portion, upper arm portion, and/or back portion of the belt portion. At least one advantage of the disclosure is that that orthopedic device is light weight and is not bulky or cumbersome, which thereby allows the user to continue doing athletic activities or normal physical activities while wearing the orthopedic device. For example, a baseball player could wear the orthopedic device underneath their baseball jersey and not interfere with the baseball player performing baseball related motions. It is customary for some athletes to wear padding underneath their jersey or uniform, in addition to being athletically taped for an injured area and/or body part. However, some athletes perform and/or compete under various environmental conditions, such as rain, snow, heat, etc., and the environment can cause the athletic tape to come off and/or lose its effectiveness, resulting in the reapplication of athletic tape. The orthopedic device does not lose its effectiveness due to the environment, and thereby eliminates the need to apply and/or reapply athletic tape.

Although the disclosure has been described in considerable detail with reference to certain configurations thereof, other variations are possible. Orthopedic devices according to the disclosure can be many different sizes and can be used to support many different joints, and is not intended to be limited to shoulder joints. In other aspects, the orthopedic device can be configured to support a knee joint, wherein the orthopedic device comprises an anchoring portion, an upper leg portion, and a support system, wherein the orthopedic device provides support and/or stability to a knee joint allowing for substantially a full range of motion of the knee joint. The orthopedic device can be configured to support various joints. In such aspects, the orthopedic device comprises an anchoring portion to anchor the orthopedic device proximate the joint, a support region opposite the anchoring portion, and a support system, such that the anchoring portion, support region and support system cooperate with each other to support and/or stabilize the joint.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

We claim:

1. An orthopedic device, comprising:
    a torso portion, comprising:
        a belt portion adapted to secure the orthopedic device to a torso; and
        a shoulder portion adapted to be removably coupled to the belt portion;
    an upper arm portion proximate the torso portion, the upper arm portion comprising:
        an inner upper arm portion; and
        an outer upper arm portion, wherein the inner and outer upper arm portions are adapted to secure the orthopedic device to an upper arm; and a support system coupled to at least part of the torso portion and part of the upper arm portion, wherein the support system is adapted to stabilize the upper arm within a shoulder joint throughout a range of upper arm motion, wherein the support system comprises at least a first strap having a first end and a second end, wherein the first end is coupled to part of the upper arm portion and the second end is coupled to part of the torso portion, wherein the support system comprises at least a second strap having a first end and a second end, wherein the first end of the second strap is coupled to part of the torso portion proximate the shoulder portion and the second end of the second strap is coupled to part of the torso portion proximate the belt portion, wherein at least one resistance band is received by the first strap, and at least one resistance band is received by the second strap.

2. The orthopedic device of claim 1, the belt portion comprising:
 a front portion;
 a back portion, wherein the front and back portions are adapted to be removably coupled to each other.

3. The orthopedic device of claim 2, wherein the shoulder portion comprises a shoulder band configured to be removably coupled to the back portion.

4. The orthopedic device of claim 2, wherein the back portion is comprised of a plurality of back portions, wherein a first back portion is removably coupled to the front portion and to a second back portion, wherein the second back portion is removably coupled to the front portion.

5. The orthopedic device of claim 1, wherein the upper arm portion is coupled to the torso portion proximate the shoulder portion.

6. The orthopedic device of claim 1, wherein the support system exerts a force onto at least the shoulder joint to assist in alignment of the upper arm within the shoulder joint during the range of upper arm motion.

7. The orthopedic device of claim 1, wherein the first strap extends between the upper arm portion and the torso portion along a rear region of the torso portion.

8. The orthopedic device of claim 1, wherein the support system further comprises at least one resistance band, wherein the at least one resistance band is received by the first strap.

9. The orthopedic device of claim 8, wherein the support system further comprises a resistance band housing, wherein part of the at least one resistance band is received by the resistance band housing.

10. The orthopedic device of claim 9, wherein the resistance band housing is removably coupled to a rear region of the torso portion.

11. The orthopedic device of claim 1, wherein each of the at least one resistance band received by the first and second straps is configured to provide a resistance force to stabilize the upper arm within the shoulder joint.

12. The orthopedic device of claim 1, wherein part of the at least one resistance band of the first and second straps is received by a resistance band housing.

13. The orthopedic device of claim 12, wherein the resistance band housing assists in positioning the at least one resistance band of the first and second straps.

14. The orthopedic device of claim 13, wherein the resistance band housing is removably coupled to a rear region of the torso portion, such that the arrangement of the at least one resistance band of the first and second straps can be adjusted.

15. The orthopedic device of claim 14, wherein the arrangement of the at least one resistance band of the first and second straps is substantially maintained by the resistance band housing.

16. An orthopedic device, comprising:
 a torso portion, comprising:
  a belt portion comprising a plurality of belt portion panels, wherein the plurality of belt portion panels are adapted to be removably coupled such that the size of the belt portion is adjustable; and
  a shoulder portion comprising at least one front shoulder band portion and a back shoulder band portion, wherein the at least one front shoulder band portion is removably coupled to the belt portion, wherein the back shoulder band portion extends from the belt portion and is fixedly attached to the at least one front shoulder band portion;
 an upper arm portion coupled to the shoulder portion, the upper arm portion comprising:
  an inner upper arm portion;
  an outer upper arm portion; and
  at least one opening such that the upper arm portion can move with respect to the shoulder portion; and
 a support system coupled to at least part of the shoulder portion, part of the upper arm portion, and removably coupled to part of the belt portion, wherein the support system is adapted to exert a force proximate the shoulder portion in order to promote biomechanical stability.

17. The orthopedic device of claim 16, the support system comprising:
 at least a first strap having a first end and a second end, wherein the first end is coupled to part of the upper arm portion and the second end is removably coupled to part of the belt portion;
 at least a second strap having a first end and a second end, wherein the first end of the second strap is coupled to part of the shoulder portion and the second end of the second strap is removably coupled to part of the belt portion;
 at least one resistance band, where the at least one resistance band comprises at least one first resistance band received by the first strap, and at least one second resistance band received by the second strap; and
 a resistance band housing comprising a plurality of channels, wherein part of each of the at least one first and second resistance bands is received within a respective channel, wherein the arrangement of the first and second straps is substantially maintained by the resistance band housing.

* * * * *